(12) United States Patent
Askem et al.

(10) Patent No.: US 12,329,896 B2
(45) Date of Patent: Jun. 17, 2025

(54) SYSTEMS AND METHODS FOR EXTENDING OPERATIONAL TIME OF NEGATIVE PRESSURE WOUND TREATMENT APPARATUSES

(71) Applicant: T.J. Smith and Nephew, Limited, Hull (GB)

(72) Inventors: Ben Alan Askem, Leeds (GB); John Philip Gowans, Hessle (GB); William Kelbie, Inverness (GB); Damyn Musgrave, Cottenham (GB); Roberto Damiao Da Costa Rodrigues, Hull (GB); Daniel Lee Steward, Hull (GB)

(73) Assignee: T.J. Smith and Nephew, Limited, Hull (GB)

( * ) Notice: Subject to any disclaimer, the term of this patent is extended or adjusted under 35 U.S.C. 154(b) by 0 days.

(21) Appl. No.: 18/641,163

(22) Filed: Apr. 19, 2024

(65) Prior Publication Data
US 2024/0269369 A1    Aug. 15, 2024

Related U.S. Application Data

(63) Continuation of application No. 17/613,456, filed as application No. PCT/EP2020/064601 on May 26, 2020, now Pat. No. 12,005,182.

(30) Foreign Application Priority Data

May 31, 2019  (GB) ...................... 1907716

(51) Int. Cl.
*A61M 1/00*      (2006.01)
*A61F 13/05*     (2024.01)

(52) U.S. Cl.
CPC ............. *A61M 1/962* (2021.05); *A61F 13/05* (2024.01); *A61M 2205/16* (2013.01); *A61M 2205/3344* (2013.01); *A61M 2205/82* (2013.01)

(58) Field of Classification Search
None
See application file for complete search history.

(56) References Cited

U.S. PATENT DOCUMENTS

2008/0243079 A1* 10/2008 Wooley ............. A61M 5/14244
                                                      324/426
2015/0051560 A1*  2/2015 Askem ................... A61M 1/74
                                                      604/319
2017/0368239 A1* 12/2017 Askem ..................... A61M 1/96

* cited by examiner

*Primary Examiner* — Rebecca E Eisenberg
*Assistant Examiner* — Katherine-Ph Minh Pham
(74) *Attorney, Agent, or Firm* — Knobbe, Martens, Olson & Bear, LLP

(57) ABSTRACT

A negative pressure wound therapy system can include a source of negative pressure negative pressure configured to aspirate fluid from a wound covered by a wound dressing and electronic circuitry with a power source, boost converter circuitry configured to receive power at a first level from the power source and supply power at a second level to the source of negative pressure, the second level being higher than the first level, and a controller configured to, in response to a determination that a capacity of the power source is being depleted, cause the boost converter circuitry to supply power to the source of negative pressure at a third level lower than the second level. The controller can further lower a target negative pressure level associated with negative pressure provided by the source of negative pressure.

20 Claims, 15 Drawing Sheets

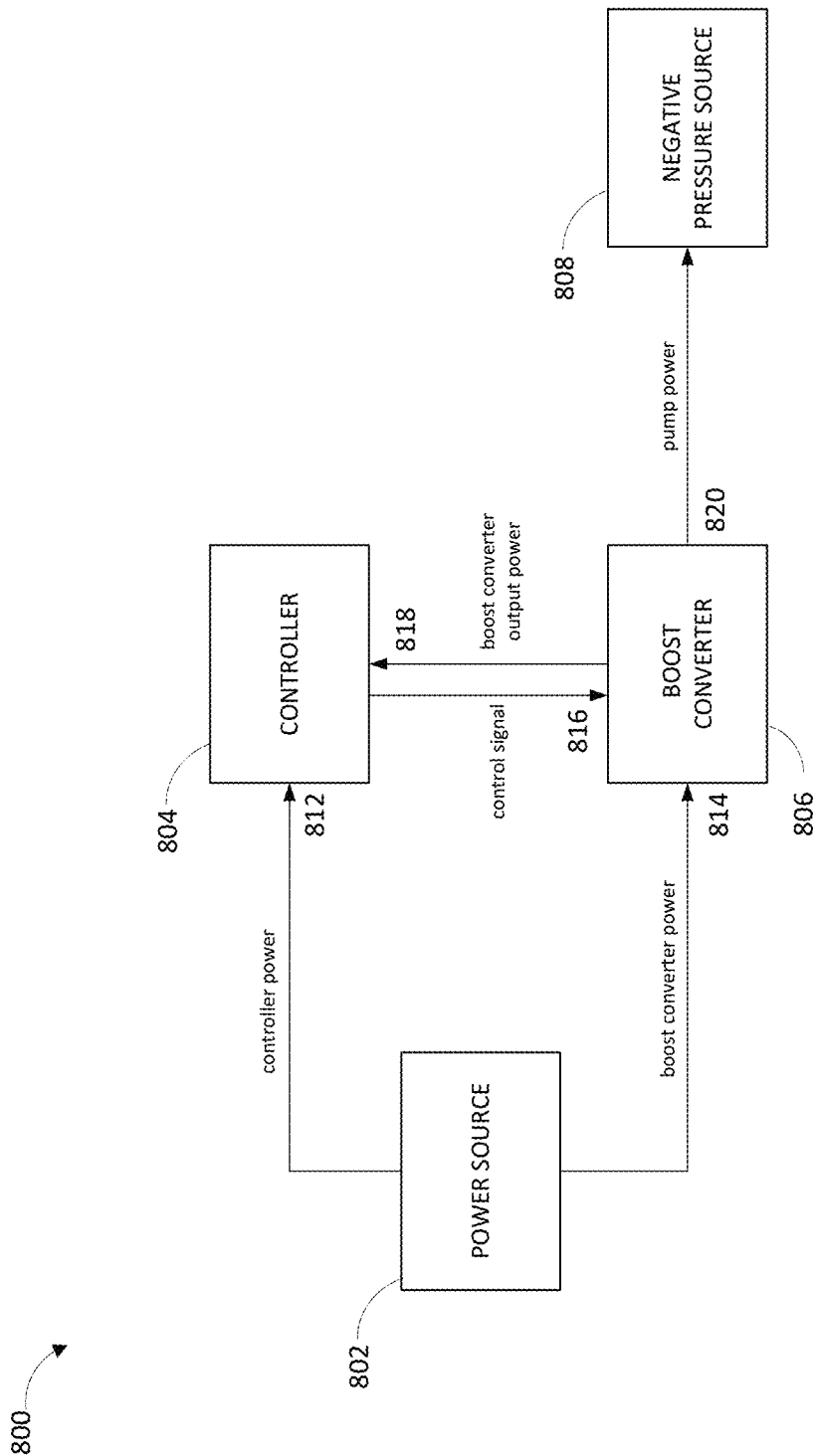

SYSTEMS AND METHODS FOR EXTENDING OPERATIONAL TIME OF NEGATIVE PRESSURE WOUND TREATMENT APPARATUSES

CROSS-REFERENCE TO RELATED APPLICATIONS

This application is a continuation of U.S. application Ser. No. 17/613,456, filed Nov. 22, 2021, which is a U.S. national stage application of International Patent Application No. PCT/EP2020/064601, filed May 26, 2020, which claims priority to Great Britain Patent Application No. 1907716.3, filed May 31, 2019, each of which is hereby incorporated by reference in its entirety and made part of this disclosure.

TECHNICAL FIELD

Embodiments described herein relate to apparatuses, systems, and methods the treatment of wounds, for example using dressings in combination with negative pressure wound therapy.

DESCRIPTION OF THE RELATED ART

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

SUMMARY

A negative pressure wound therapy system can include a wound dressing configured to be placed over a wound of a patient, the wound dressing configured to absorb fluid, a source of negative pressure disposed on or within the dressing, the source of negative pressure configured to aspirate fluid from the wound, a power source disposed on or within the dressing, and electronic circuitry disposed on or within the dressing. The electronic circuitry can include boost converter circuitry configured to receive power at a first level from the power source and output power at a second level to the source of negative pressure, the second level being higher than the first level. The electronic circuitry can include a controller configured to monitor capacity of the power source and, in response to a determination that the capacity of the power source is depleting, provide a first control signal to cause the boost converter circuitry to output power to the source of negative pressure at a third level lower than the second level.

The system of any of the preceding paragraphs and/or any of the systems disclosed herein can include one or more of the following features. The controller can be configured to monitor the capacity of the power source by at least one of monitoring power supplied to the controller by the power source or monitoring the power output of the boost converter circuitry. Determination that the capacity of the power source is depleting can include a determination that the power output by the boost converter circuitry is below the second level of power. Provision of the first control signal to cause the boost converter circuitry to output power to the source of negative pressure at the third level can cause the source of negative pressure to provide a lower level of negative pressure to the wound than a negative pressure level associated with the boost converter circuitry outputting the power to the source of negative pressure at the second level. The controller can be configured to, in response to a determination that the capacity of the power source is continuing to deplete, provide a second control signal to cause the boost converter circuitry to output power to the source of negative pressure at a fourth level lower than the third level. The controller can be configured to, in response to a subsequent determination that the capacity of the power source is continuing to deplete, provide a third control signal to cause the boost converter circuitry to output power to the source of negative pressure at a fifth level, the fifth level associated with a lowest level of power provided to the source of negative pressure. The controller can be configured to, in response to a determination that the capacity of the power source satisfies a depletion threshold, transition to a non-operational state in which the system ceases to provide negative pressure wound therapy. The system can include at least one indicator, and the controller can be configured to cause the at least one indicator to indicate transition to the non-operational state.

The system of any of the preceding paragraphs and/or any of the systems disclosed herein can include one or more of the following features. The controller can be configured to, in response to a determination that a duration of time since initial activation satisfies a lifetime threshold, transition to the non-operational state. The controller can be configured to, in response to the determination that the capacity of the power source is depleting, disable leak detection. The controller can be configured to disable leak detection in response to a determination that the power output by the boost converter circuitry is below the second level of power.

A negative pressure wound therapy system can include a source of negative pressure negative pressure configured to aspirate fluid from a wound covered by a wound dressing, a power source, boost converter circuitry configured to receive power at a first level from the power source and supply power at a second level to the source of negative pressure, the second level being higher than the first level, and a controller configured to, in response to a determination that a capacity of the power source is being depleted, cause the boost converter circuitry to supply power to the source of negative pressure at a third level lower than the second level.

The system of any of the preceding paragraphs and/or any of the systems disclosed herein can include one or more of the following features. Determination that the capacity of the power source is being depleted can include a determination that the power supplied by the boost converter circuitry is below the second level of power. The controller can be configured to operate the source of negative pressure to provide negative pressure at a target negative pressure level and, in response to the determination that the capacity of the power source is being depleted, lower the target negative pressure level. The controller can be configured to, in response to a determination that the capacity of the power source is continuing to deplete, cause the boost converter circuitry to supply power to the source of negative pressure at a fourth level lower than the third level. The controller can be configured to, in response to a subsequent determination that the capacity of the power source is continuing to deplete, cause the boost converter circuitry to supply power to the source of negative pressure at a fifth level, the fifth level associated with a lowest level of power provided to the source of negative pressure. The controller can be configured to, in response to a determination that the capacity of the power source satisfies a depletion threshold, cease operating the source of negative pressure to aspirate fluid from the wound. The system can include at least one indicator, and the controller can be configured to cause provision via the at least one indicator of an indication responsive to the determination that the capacity of the power source satisfies the depletion threshold.

A method of operating a negative pressure wound therapy system can include increasing power provided from a power source of the negative pressure wound therapy system at a first level to a second level, supplying power at the second level to a source of negative pressure negative pressure of the negative pressure wound therapy system and causing the source of negative pressure to provide negative pressure at a target negative pressure level to a wound covered by a wound dressing, and, in response to determining that a capacity of the power source is being depleted, decreasing power from the second level to a third level and supplying power to the source of negative pressure at the third level. The method can be performed under control of a controller of the negative pressure wound therapy system.

The method of any of the preceding paragraphs and/or any of the methods disclosed herein can include one or more of the following features. The method can include lowering the target negative pressure level in response to determining that the capacity of the power source is being depleted. Determining that the capacity of the power source is being depleted can include determining that increasing power provided from the power source at the first level to the second level does not produce increased power at the second level. The method can include, in response determining that the capacity of the power source is continuing to deplete, decreasing power from the third level to a fourth level and supplying power to the source of negative pressure at the fourth level. The method can include, in response to subsequently determining that the capacity of the power source is continuing to deplete, decreasing power to a minimum level of power and supplying power to the source of negative pressure at the minimum level of power. The method can include, in response to determining that the capacity of the power source satisfies a depletion threshold, stopping operation of the source of negative pressure. The method can include, in response to determining that the capacity of the power source satisfies the depletion threshold, providing an indication to a user.

BRIEF DESCRIPTION OF THE DRAWINGS

FIG. 8 illustrates a block diagram of power distribution in an electronics assembly of a negative pressure wound therapy system;

DETAILED DESCRIPTION

Figure 1A:
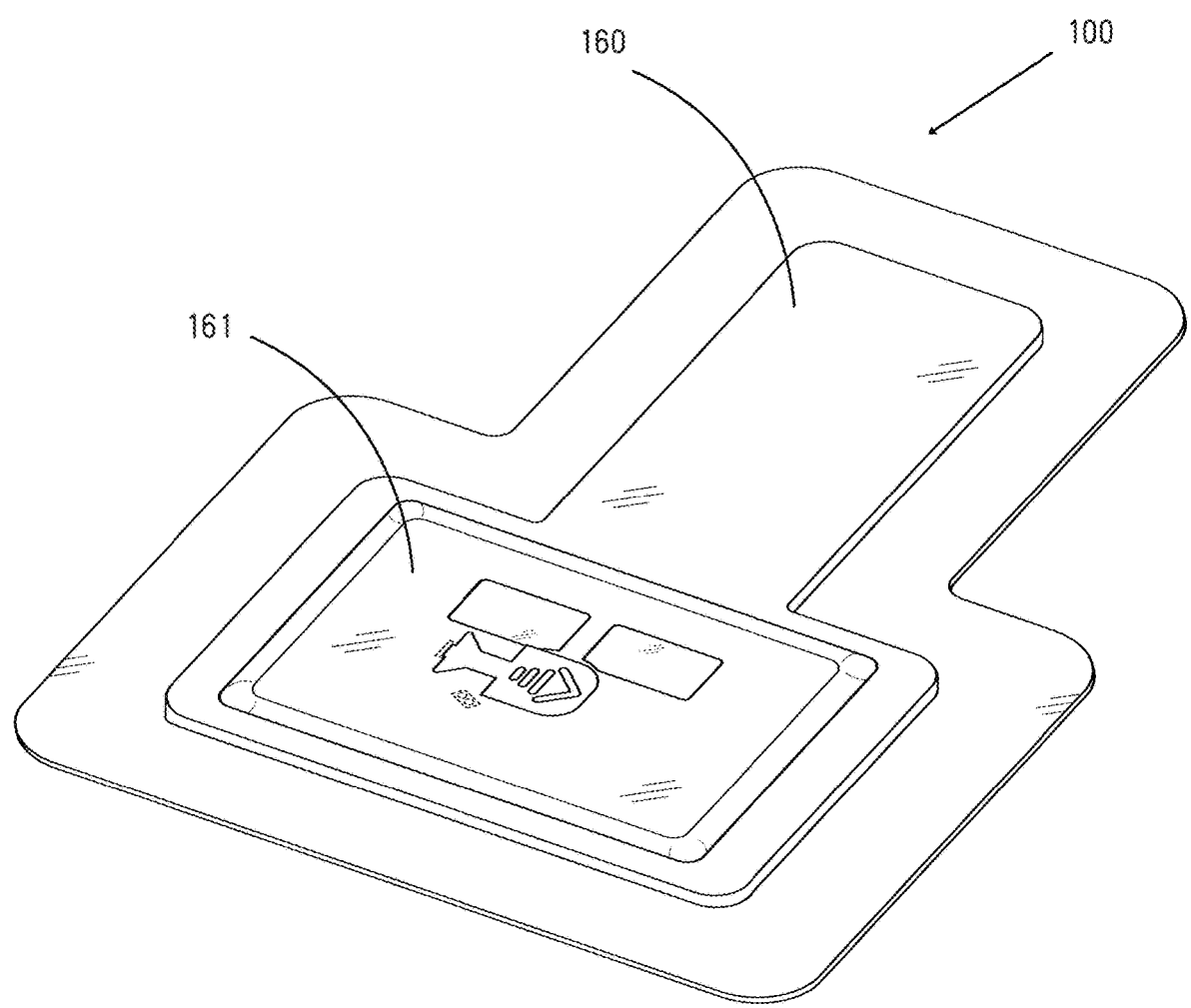
FIGS. 1A-1C illustrate a wound dressing incorporating a source of negative pressure and/or other electronic components within the wound dressing.

Embodiments disclosed herein relate to apparatuses and methods of treating a wound with reduced pressure, including a source of negative pressure and wound dressing components and apparatuses. These apparatuses and components, including but not limited to wound overlays, backing layers, cover layers, drapes, sealing layers, spacer layers, absorbent layers, transmission layers, wound contact layers, packing materials, fillers and/or fluidic connectors are sometimes collectively referred to herein as dressings.

It will be appreciated that throughout this specification reference is made to a wound. It is to be understood that the term wound is to be broadly construed and encompasses open and closed wounds in which skin may be torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in NPWT or topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, 1013.25 mbar, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some cases, local ambient atmospheric pressure is used as a reference point, and such local atmospheric pressure may not necessarily be, for example, 760 mmHg.

The negative pressure range can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the negative pressure apparatus.

Wound Dressing

Figure 1B:
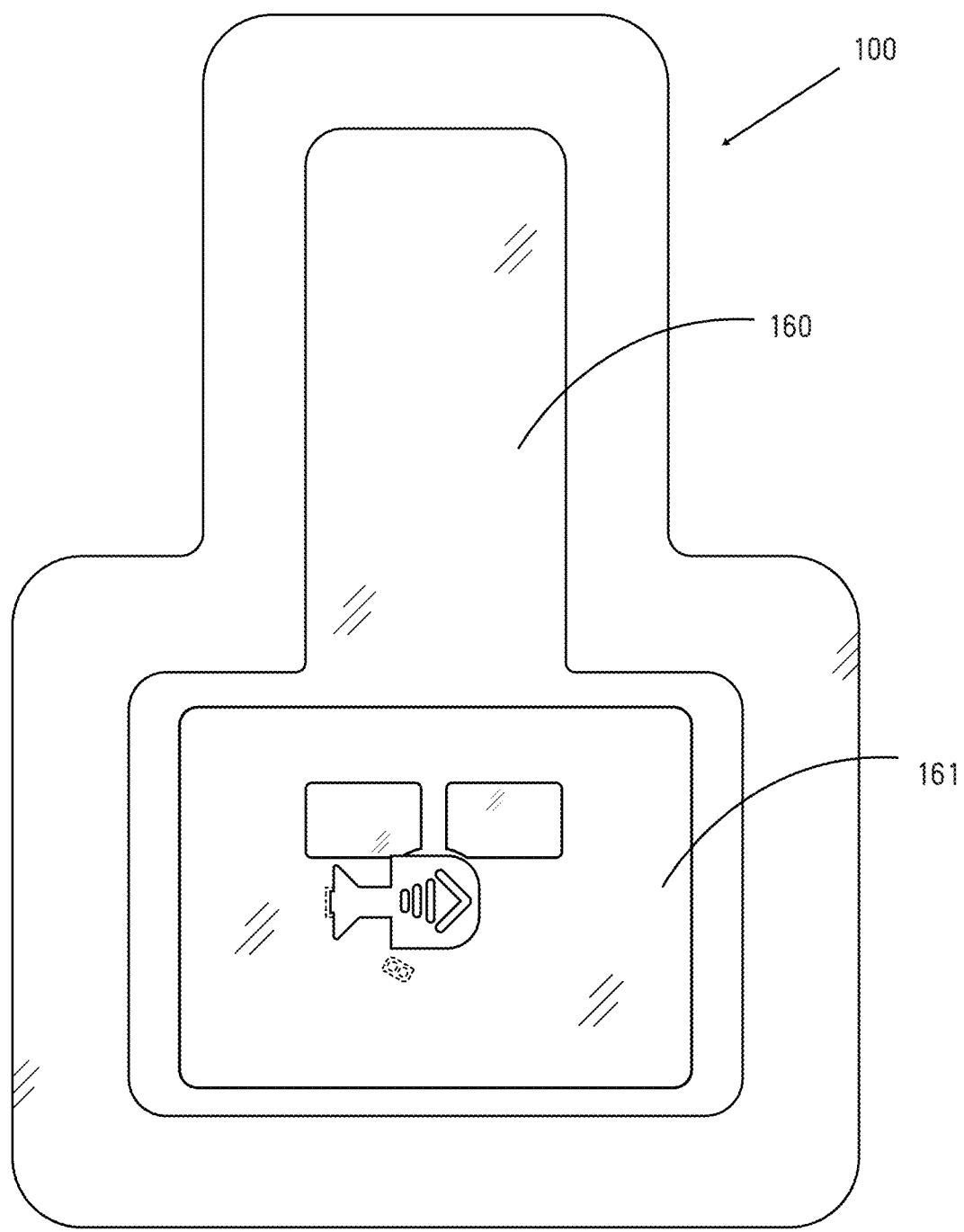
Figure 1C:
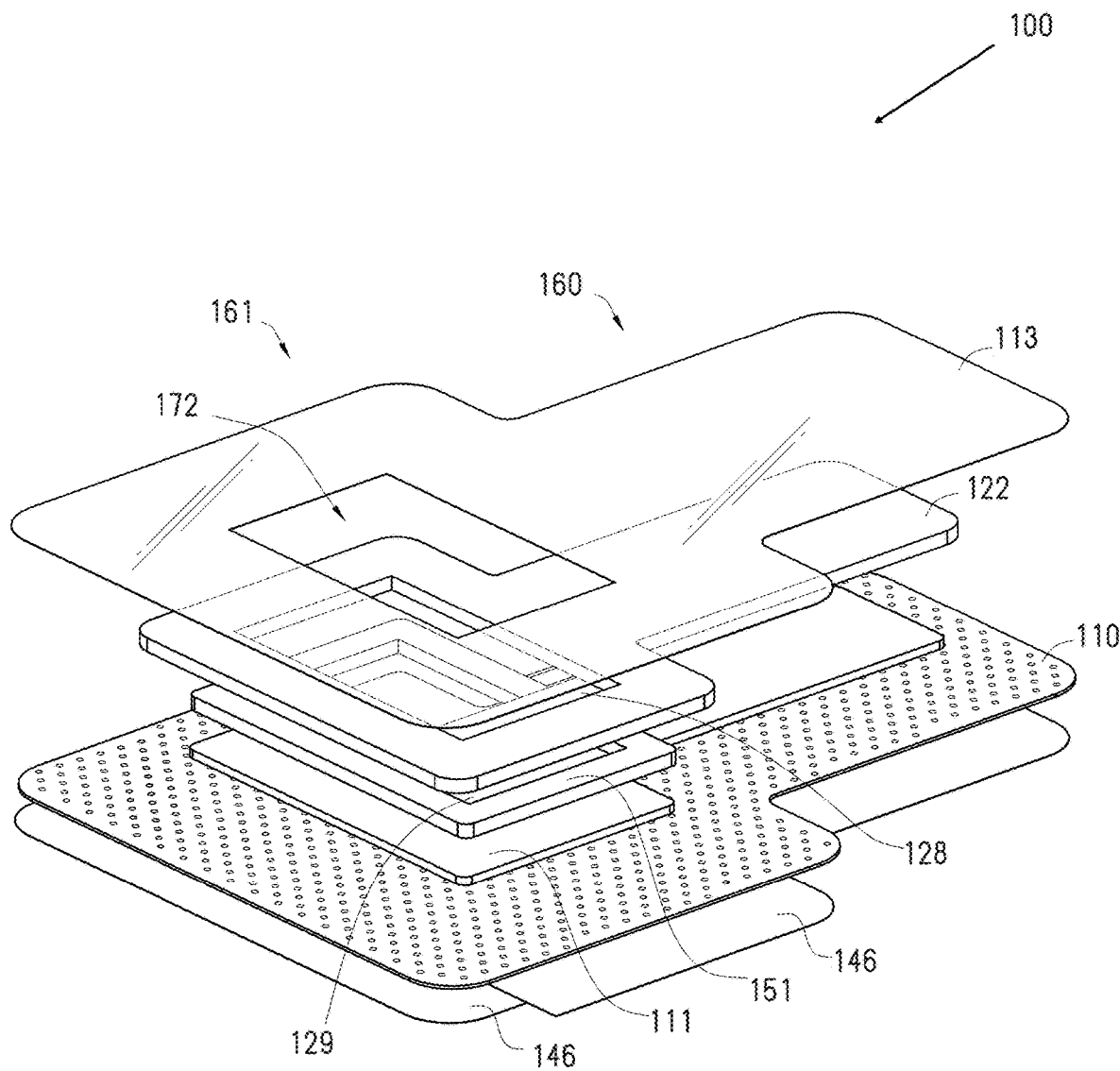

A source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The material layers can include a wound contact layer, one or more absorbent layers, one or more transmission or spacer layers, and a backing layer or cover layer covering the one or more absorbent and transmission or spacer layers. The wound dressing can be placed over a wound and sealed to the wound with the pump and/or other electronic components contained under the cover layer within the wound dressing. The dressing can be provided as a single article with all wound dressing elements (including the pump) pre-attached and integrated into a single unit. A periphery of the wound contact layer can be attached to the periphery of the cover layer enclosing all wound dressing elements as illustrated in FIG. 1A-1C.

The pump and/or other electronic components can be configured to be positioned adjacent to or next to the absorbent and/or transmission layers so that the pump and/or other electronic components are still part of a single article to be applied to a patient. The pump and/or other electronics can be positioned away from the wound site. Although certain features disclosed herein may be described as relating to systems and method for controlling operation of a negative pressure wound therapy system in which the pump and/or other electronic components are positioned in or on the wound dressing, the systems and methods disclosed herein are applicable to any negative pressure wound therapy system or any medical device. FIGS. 1A-1C illustrate a wound dressing incorporating the source of negative pressure and/or other electronic components within the wound dressing. FIGS. 1A-1C illustrate a wound dressing 100 with the pump and/or other electronics positioned away from the wound site. The wound dressing can include an electronics area 161 and an absorbent area 160. The dressing can comprise a wound contact layer 110 (not shown in FIGS. 1A-1B) and a moisture vapor permeable film, cover layer or backing layer 113 positioned above the contact layer and other layers of the dressing. The wound dressing layers and components of the electronics area as well as the absorbent area can be covered by one continuous cover layer 113 as shown in FIGS. 1A-1C.

A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. In particular, the transmission layer 111 preferably ensures that an open air channel can be maintained to communicate negative pressure over the wound area even when the absorbent layer has absorbed substantial amounts of exudates. The layer 111 should preferably remain open under the typical pressures that will be applied during negative pressure wound therapy as described above, so that the whole wound site sees an equalized negative pressure. The layer 111 may be formed of a material having a three dimensional structure. For example, a knitted or woven spacer fabric (for example Baltex 7970 weft knitted polyester) or a non-woven fabric could be used.

Further, one or more absorbent layers (such as layers 122, 151) for absorbing and retaining exudate aspirated from the wound can be utilized. A superabsorbent material can be used in the absorbent layers 122, 151. The one or more layers 122, 151 of absorbent material may be provided above the transmission layer 111. Since in use each of the absorbent layers experiences negative pressures, the material of the absorbent layer can be chosen to absorb liquid under such circumstances. The absorbent layers 122, 151 may comprise a composite comprising superabsorbent powder, fibrous material such as cellulose, and bonding fibers. The composite can be an airlaid, thermally-bonded composite.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch (shown in FIGS. 1A-1B as being covered by a pull tab). The button or switch can be used for operating the pump (such as, turning the pump on/off).

The electronics area 161 of the dressing can comprise one or more layers of transmission or spacer material and/or absorbent material and electronic components can be embedded within the one or more layers of transmission or spacer material and/or absorbent material. The layers of transmission or absorbent material can have recesses or cut outs to embed the electronic components within whilst providing structure to prevent collapse. As shown in FIG. 1C, recesses 128 and 129 can be provided in absorbent layers 151 and 122, respectively.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound. Additionally, the layers can have a proximal wound-facing face referring to a side or face of the layer closest to the skin or wound and a distal face referring to a side or face of the layer furthest from the skin or wound.

The cover layer may include a cutout 172 positioned over at least a portion of the aperture 128 in the absorbent layer 122 to allow access and fluid communication to at least a portion of the absorbent layers 122 and 151, transmission layer 111, and would contact layer 110 positioned below. An electronics assembly such as described below can be positioned in the apertures 128, 129, and 172 of the first and second absorbent material 151 and 122 and the cover layer 113. The electronics assembly can include a pump, power source, and a printed circuit board as described with reference to FIGS. 3 and 4A-4B.

Before use, the dressing can include one or more delivery layers 146 adhered to the bottom surface of the wound contact layer. The delivery layer 146 can cover adhesive or apertures on the bottom surface of the wound contact layer 110. The delivery layer 146 can provided support for the dressing and can assist in sterile and appropriate placement of the dressing over the wound and skin of the patient. The delivery layer 146 can include handles that can be used by the user to separate the delivery layer 146 from the wound contact layer 110 before applying the dressing to a wound and skin of a patient.

Electronics Assembly Incorporated Within the Wound Dressing

Figure 2B:
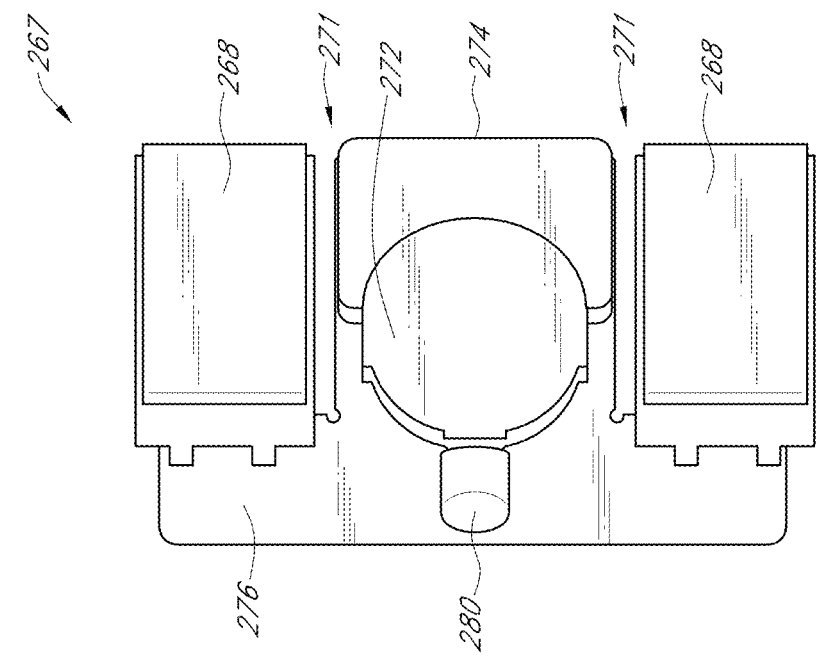
FIGS. 2A-2B illustrate an electronics unit that may be incorporated into a wound dressing.
Figure 2A:
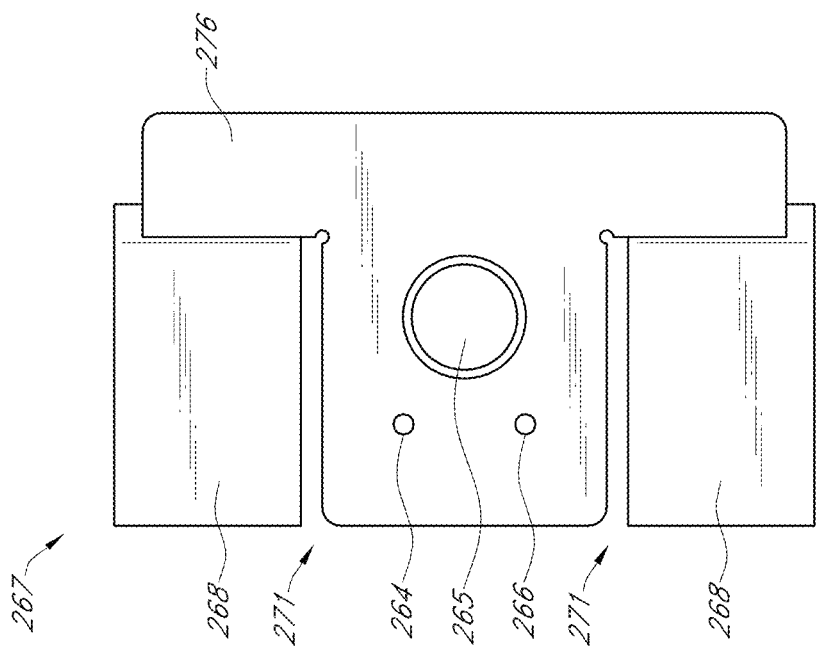

FIGS. 2A-2B illustrate an electronics unit 267 that can be incorporated into a wound dressing. FIG. 2A illustrates the top view of the electronics unit. FIG. 2B illustrates a bottom or wound facing surface of the electronics unit. The electronics unit 267 can include a pump 272 and one or more power sources 268, such as batteries. The electronics unit 267 can include a circuit board 276 configured to be in electrical communication with the pump 272 and/or power source 268. The circuit board 276 can be flexible or substantially flexible.

As illustrated in FIG. 2A, the electronics unit 267 can include single button or switch 265 on the upper surface of the unit. The single button or switch 265 can be used as an on/off button or switch to stop and start operation of the pump and/or electronic components. The electronics unit 267 can also include one or more vents or exhaust apertures 264 on the circuit board 276 for expelling the air exhausted from the pump. As shown in FIG. 2B, a pump outlet exhaust mechanism 274 (sometimes referred to as pump exhaust mechanism or pump outlet mechanism) can be attached to the outlet of the pump 272.

The electronics unit 267 can include a pump inlet protection mechanism 280 as shown in FIG. 2B positioned on the portion of the electronics unit closest to the absorbent area and aligned with the inlet of the pump 272. The pump inlet protection mechanism 280 is positioned between the pump inlet and the absorbent area or absorbent layer of the dressing. The pump inlet protection mechanism 280 can include hydrophobic material to prevent fluid from entering the pump 272. The pump inlet protection mechanism 280 (or any of the inlet protection mechanisms disclosed herein) can include a filter.

The upper surface of the electronics unit 267 can include one or more indicators 266 for indicating a condition of the pump and/or level of pressure within the dressing. The indicators can be small LED lights or other light source that are visible through the dressing components or through holes in the dressing components above the indicators. The indicators can be green, yellow, red, orange, or any other color. For example, there can be two lights, one green light and one orange light. The green light can indicate the device is working properly and the orange light can indicate that there is some issue with the pump (such as, leak, saturation level of the dressing, blockage downstream of the pump, exhaust blockage, low battery, or the like).

The power source 268 can be in electrical communication with the circuit board 276. One or more power source connections are connected to a surface of the circuit board 276. The circuit board 276 can have other electronics incorporated within. For example, the circuit board 276 may support various sensors including, but not limited to, one or more pressure sensors, temperature sensors, optic sensors and/or cameras, and/or saturation indicators.

Figure 3:
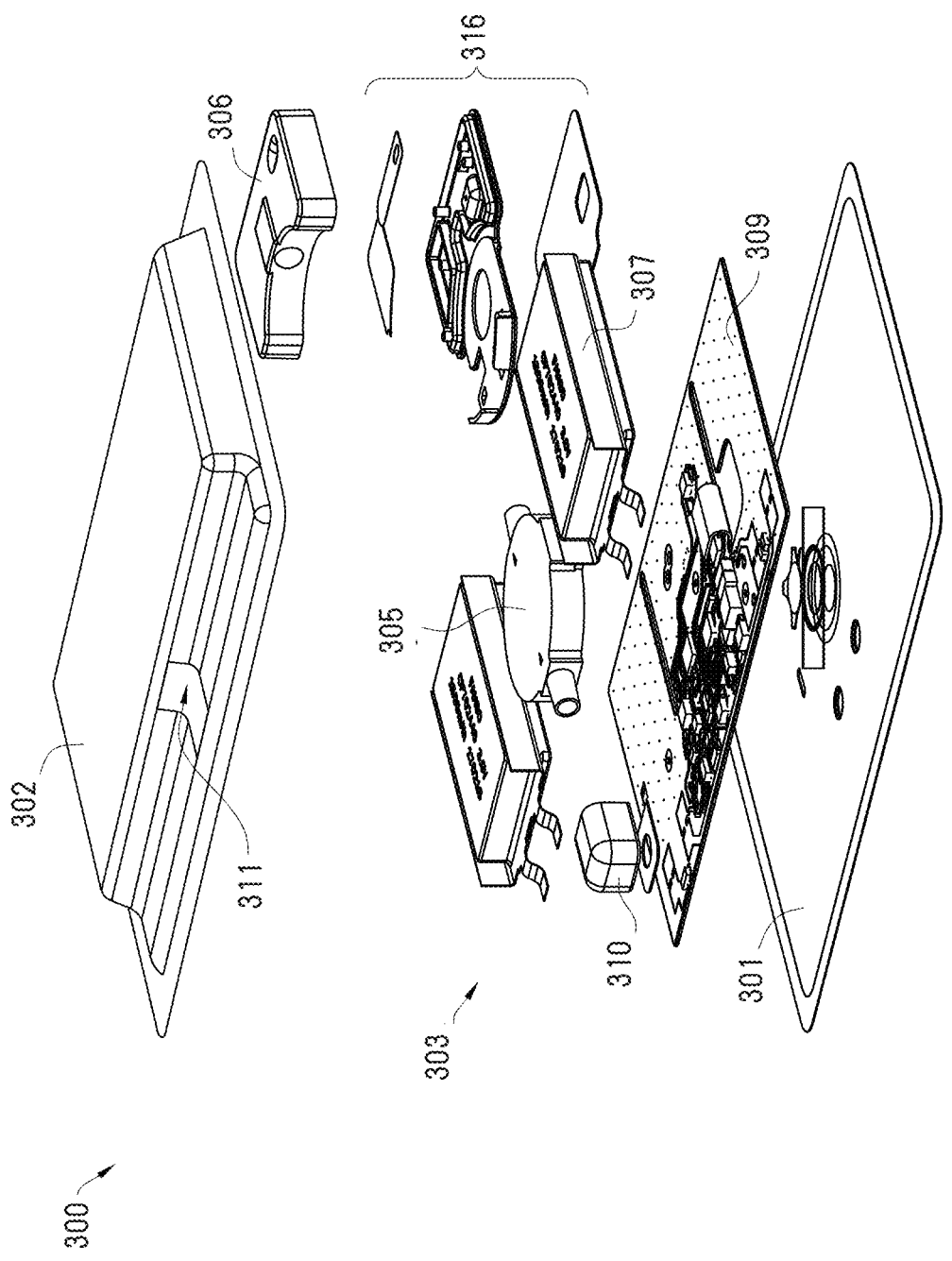
FIG. 3 is an exploded perspective view of an electronics assembly enclosing an electronics unit within a housing.

FIG. 3 illustrates an electronics assembly 300 enclosing an electronics unit within a housing. As illustrated in FIG. 3, the housing of the electronics assembly 300 can include a plate 301 and flexible film 302 enclosing the electronics unit 303 within. The electronics unit 303 can include a pump 305, inlet protection mechanism 310, pump exhaust mechanism 306, power source 307, and circuit board 309. The circuit board 309 can be flexible or substantially flexible.

As is illustrated, the pump exhaust mechanism 306 can be an enclosure, such as a chamber. The electronics unit 303 and pump 305 can be used without the inlet protection mechanism 310. However, the pump exhaust mechanism 306 and the pump 305 can sit within an extended casing 316.

The flexible film 302 can be attached to the plate 301 to form a fluid tight seal and enclosure around the electronic components. The flexible film 302 can be attached to the plate at a perimeter of the plate by heat welding, adhesive bonding, ultrasonic welding, RF welding, or any other attachment or bonding technique.

The flexible film 302 can include an aperture 311. The aperture 311 can allow the inlet protection mechanism 310 to be in fluid communication with the absorbent and/or transmission layers of the wound dressing. The perimeter of the aperture 311 of the flexible film 303 can be sealed or attached to the inlet protection mechanism 310 to form a fluid tight seal and enclosure around the inlet protection mechanism 310 allowing the electronic components 303 to remain protected from fluid within the dressing. The flexible film 302 can be attached to the inlet protection mechanism 310 at a perimeter of the inlet protection mechanism 310 by heat welding, adhesive bonding, ultrasonic welding, RF welding, or any other attachment or bonding technique. The inlet protection mechanism 310 can prevent wound exudate or liquids from the wound and collected in the absorbent area 160 of the wound dressing from entering the pump and/or electronic components of the electronics assembly 300.

The electronics assembly 300 illustrated in FIG. 3 can be incorporated within the wound dressing such that, once the dressing is applied to the body of the patient, air from within the dressing can pass through the inlet protection mechanism 310 to be pumped out toward the pump exhaust mechanism 306 in communication with an aperture in the casing 316 and the circuit board 309 as described herein.

Figure 4A:
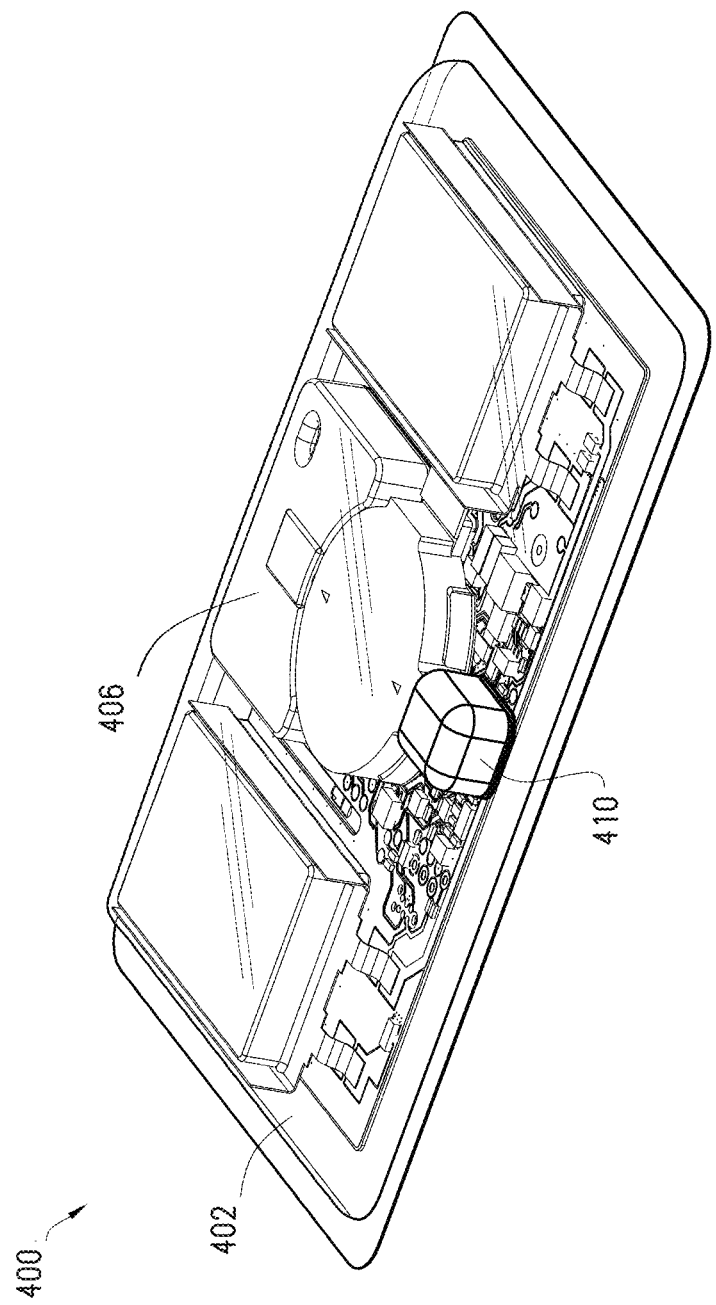
FIG. 4A illustrates a bottom perspective view of the electronics assembly of FIG. 3.
Figure 4B:
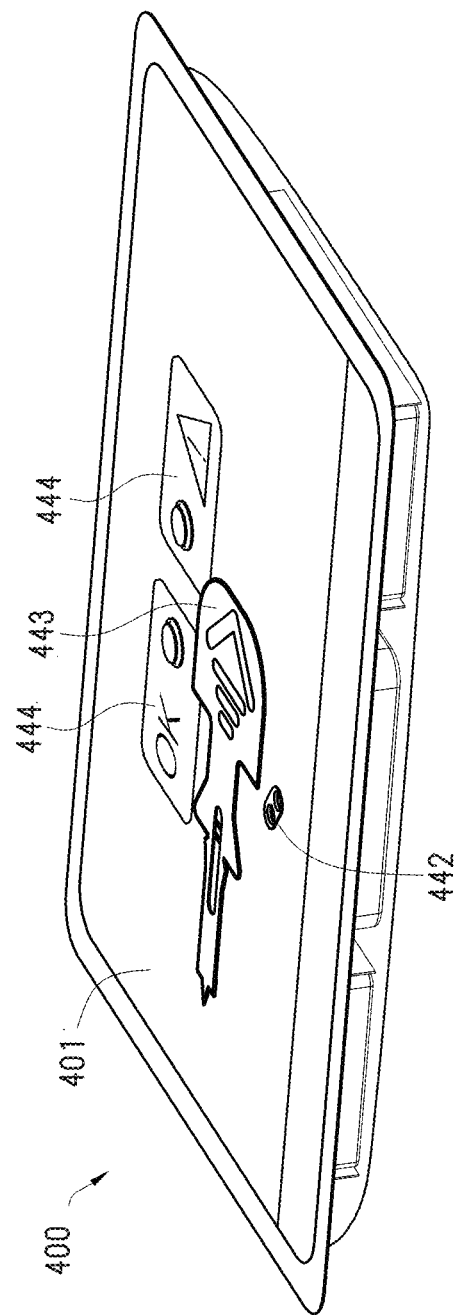
FIG. 4B illustrates a top perspective view of the electronics assembly of FIG. 3.

FIGS. 4A-B illustrate an electronics assembly 400 including a pump inlet protection mechanism 410 sealed to the exterior of the flexible film 402, similar to the description with reference to FIG. 3. Also shown is an exhaust mechanism 406, which can be similar to the exhaust mechanism 306.

FIG. 4A illustrates lower, wound facing surface of the electronics assembly 400. FIG. 4B shows an upper surface of the plate 401 (which can face the patient or user) of the electronics assembly 400. The upper surface of the plate 401 can include an on/off switch or button cover 443 (illustrated as a pull tab), indicators 444, and/or one or more vent holes 442. Removal of the pull tab 443 can cause activation of the electronics assembly 400, such as provision of power from the power source to the electronics assembly. Further details of operation of the pull tab 443 are described in PCT International Application No. PCT/EP2018/079745, filed Oct. 30, 2018, titled "SAFE OPERTATION OF INTEGRATED NEGATIVE PRESSURE WOUND TREATMENT APPARATUSES," which is incorporated by reference in its entirety herein.

The electronics assembly 400 with the pump inlet protection mechanism 410 extending from and sealed to the film 402 can be positioned within the aperture 172 in the cover layer 113 and absorbent layer(s) (122, 151) as shown in FIG. 1C. The perimeter of the electronics assembly 400 can be sealed to a top surface of the outer perimeter of the aperture 172 in the cover layer 113 as shown in FIG. 1C and described in more detail with reference to FIG. 5A-5B herein. The electronics assembly 400 can be sealed to the cover layer 113 with a sealant gasket, adhesive, heat welding, adhesive bonding, ultrasonic welding, RF welding, or any other attachment or bonding technique. The electronics assembly 400 can be permanently sealed to the cover layer 113 and could not be removed from the cover layer without destroying the dressing.

The electronics assembly 400 can be utilized in a single dressing and disposed of with the dressing. In some cases, the electronics assembly 400 can be utilized in a series of dressings.

Figure 5A:
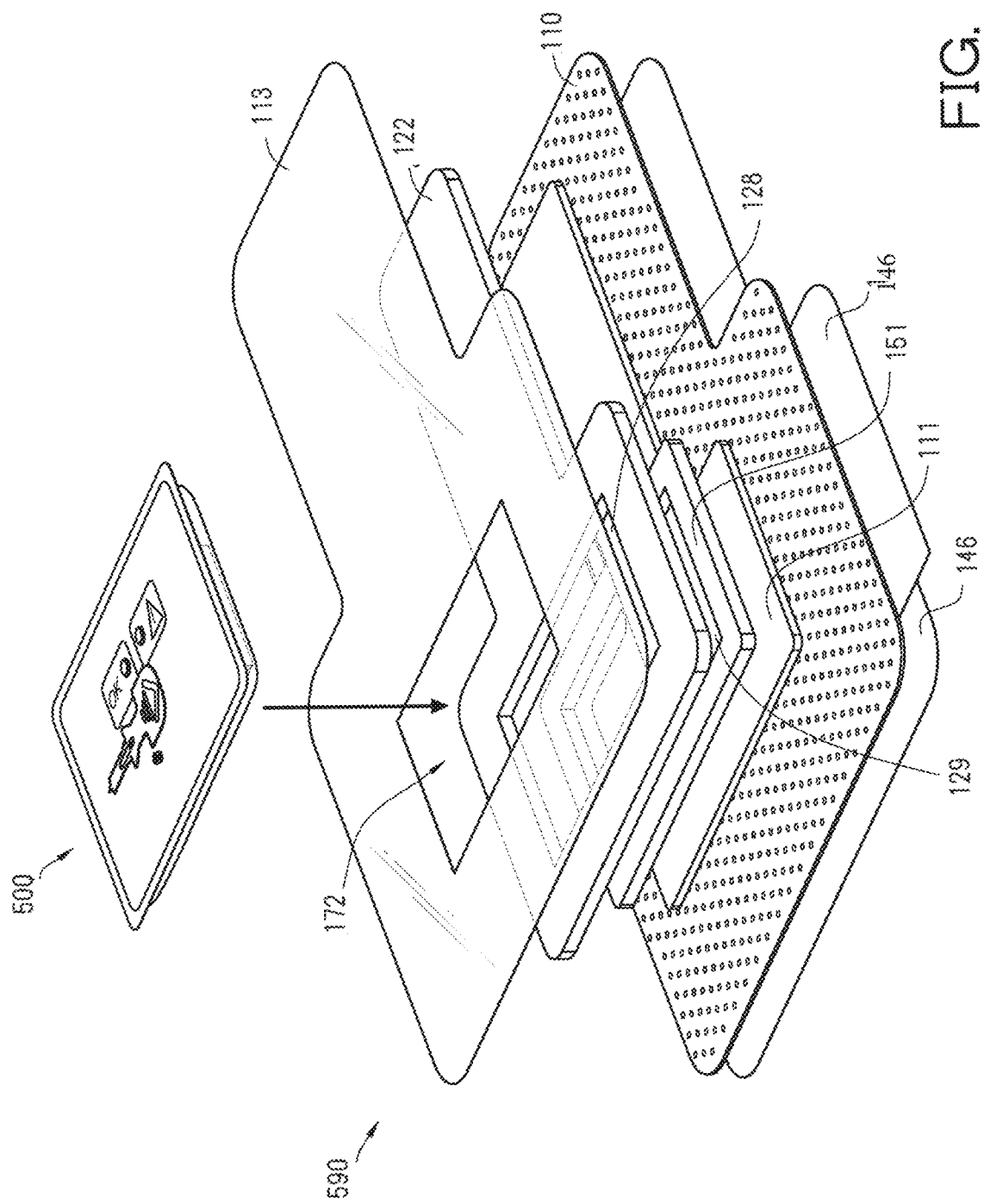
FIG. 5A is an exploded view of a wound dressing incorporating an electronics assembly within the wound dressing layers.
Figure 5B:
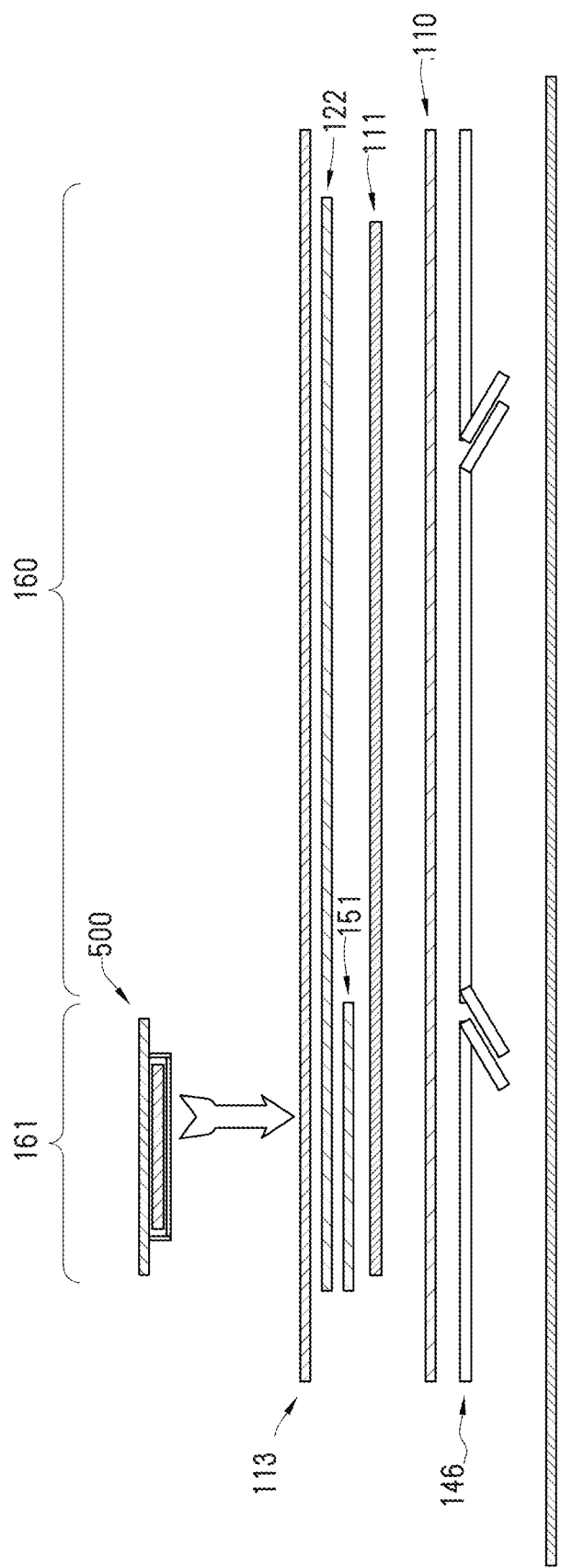
FIG. 5B illustrates a cross sectional layout of the material layers of a wound dressing incorporating an electronics assembly within the dressing.

FIG. 5A illustrates a wound dressing, such as the one in FIG. 1C, incorporating an electronics assembly 500 within the wound dressing layers 590. FIG. 5B illustrates a cross-sectional view of the wound dressing incorporating the electronics assembly of FIG. 5A. The electronics assembly 500 can be provided within the aperture 172 in the cover layer and apertures 129 and 128 in the first and second absorbent layers 122, 151. The electronics assembly 500 can seal to the outer perimeter of the aperture 172 of the cover layer. The dressing can comprise a wound contact layer 110 and a moisture vapor permeable film, cover layer or backing layer 113 positioned above the contact layer 110 and other layers of the dressing. A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. Further, one or more absorbent layers (such as layers 122, 151) for absorbing and retaining exudate aspirated from the wound can be utilized. The one or more layers 122, 151 of absorbent material may be provided above the transmission layer 111. There may be a small aperatured absorbent layer 151 and a large aperture absorbent layer 122. The small apertured absorbent layer 151 can be positioned on top of the large apertured absorbent layer 122. In some cases, the small apertured absorbent layer 151 can be positioned below of the large apertured absorbent layer 122. Before use, the dressing can include one or more delivery layers 146 adhered to the bottom surface of the wound contact layer. The delivery layer 146 can cover adhesive or apertures on the bottom surface of the wound contact layer 110.

FIGS. 6A-6B and 7A-7B illustrate an electronics assembly 600 with a pump inlet protection mechanism 610 and pump exhaust mechanism 674 on a pump 672. The assembly 600 can include cavities 682 and 683 (shown in FIGS. 7A-7B) on the pump inlet protection mechanism 610 and pump exhaust mechanism 674, respectively. The inlet protection and pump exhaust mechanisms can be adhered to the inlet and the outlet of the pump as described herein. The assembly 600 can be assembled using an adhesive and allowed to cure prior to incorporating into the electronics assembly. The assembly can include a power source, such as two batteries 668.

The pump inlet can be covered or fitted with a pump inlet protection mechanism 610. The pump inlet protection 610 can be pushed onto the pump inlet as illustrated by the arrows in FIG. 7A. This can be a friction fit. The port of the pump inlet protection 610 that receives a portion of the pump inlet can be sized and shaped to be a complementary fit around the pump inlet. The pump inlet protection 610 can be bonded onto the pump inlet using a silicone sealant or any other sealant or sealing technique. FIG. 7B illustrates the pump inlet protection mechanism 610 covering the pump inlet and the pump exhaust mechanism 674 covering the pump outlet. The pump exhaust mechanism 674 can include one or more apertures or vents 684 to allow gas aspirated by the pump to be exhausted from the pump exhaust mechanism 674. In some cases, a non-return valve and/or filter membrane of the pump exhaust mechanism is included in the pump exhaust mechanism 674.

Figure 6A:
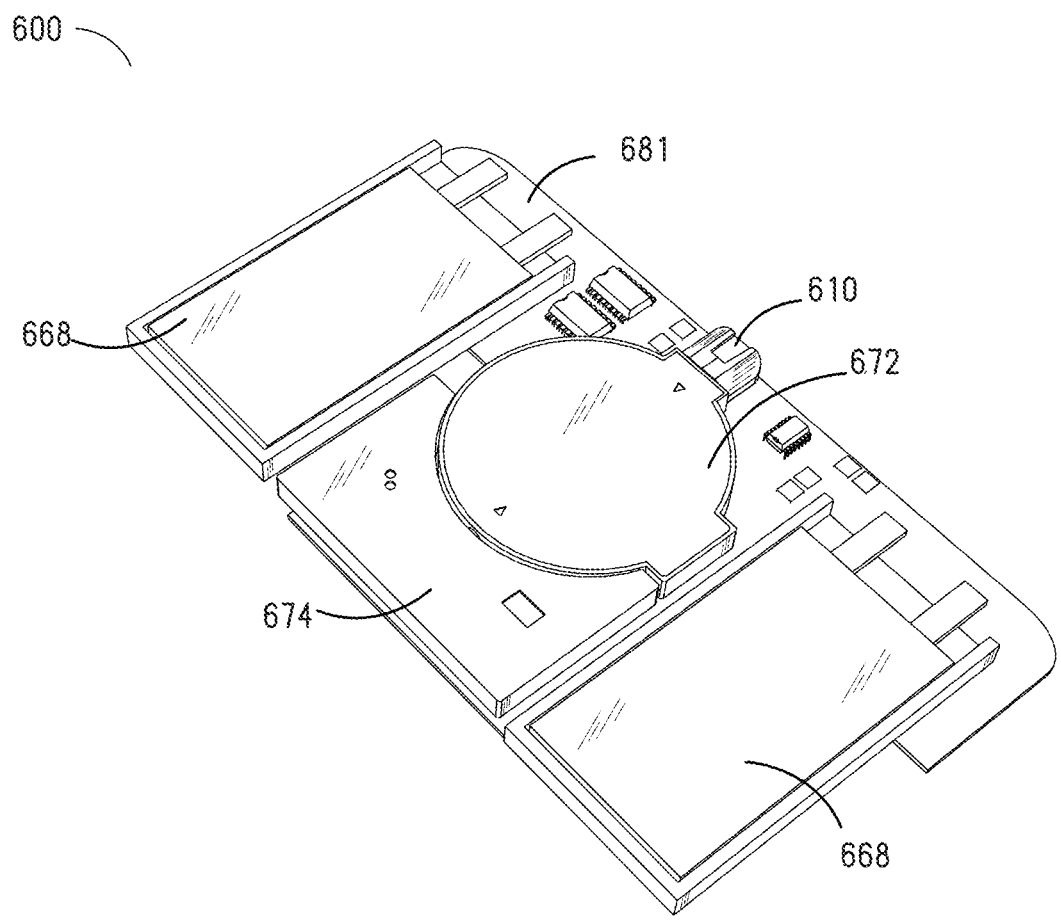
FIGS. 6A-6B and 7A-7B illustrate components of an electronics assembly.
Figure 6B:
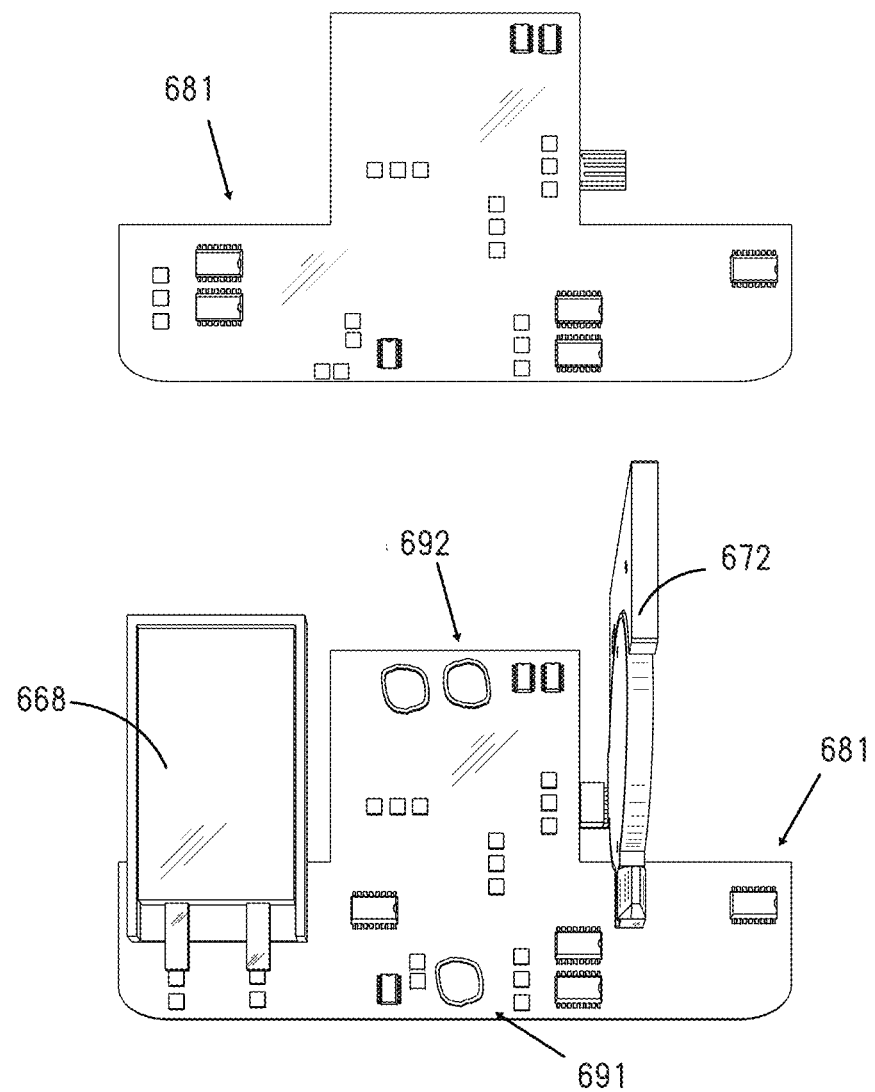
Figure 7A:
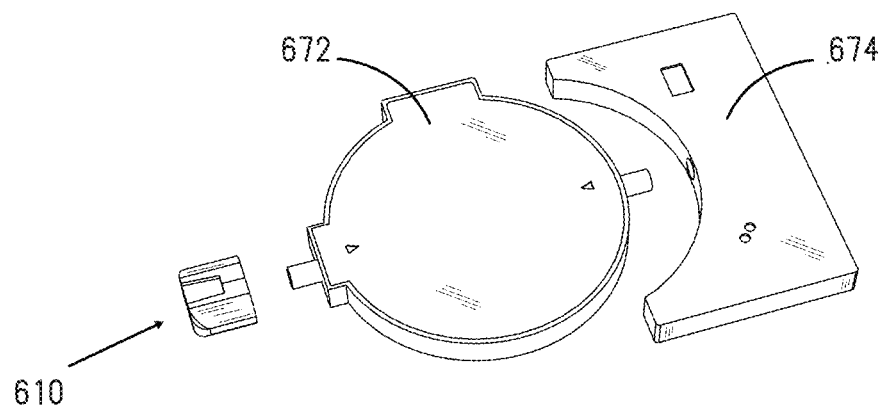
Figure 7B:
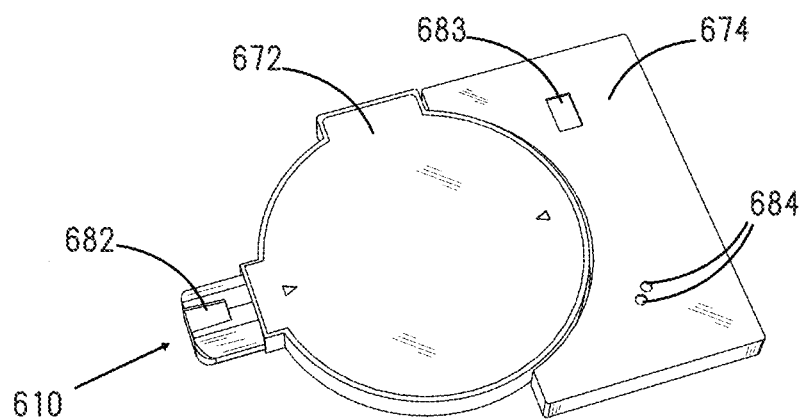

FIGS. 7A-7B illustrate the pump inlet protection mechanism 610 and pump exhaust mechanism 674 with cavities 682 and 683. A pump assembly including the pump inlet protection mechanism 610 and pump exhaust mechanism 674 can be placed over the surface of a circuit board 681. When the pump assembly is in contact with the surface of the circuit board 681, the cavities 682 and 683 can at least partially enclose sensors on the circuit board 681, for example, pressure sensors 691 and 692 on the circuit board 681, as illustrated in FIG. 6B.

The pressure sensors 691 and 692 illustrated in FIG. 6B can be used to measure and/or monitor the pressure level at the wound and atmospheric pressure. The pressure sensor 691 can be used to measure and/or monitor pressure at the wound (such as, underneath the wound dressing), which can be accomplished by measuring and/or monitoring pressure in a fluid flow path connecting the negative pressure source or pump 672 and the wound. The pressure sensor 691 can measure and/or monitor pressure in the cavity 682 of the pump inlet protection mechanism 610 shown in FIGS. 7A-7B.

The pressure sensor 692 can be used to measure and/or monitor pressure external to the wound dressing. The pressure sensor 692 can measure and/or monitor pressure in the cavity 683 of the pump exhaust mechanism 674 shown in FIGS. 7A-7B. The pressure sensor 692 can measure pressure external to the wound dressing, which can be relative atmospheric pressure since the atmospheric pressure varies depending on, for instance, an altitude of use or pressurized environment in which the TNP apparatus may be used. These measurements can be used to establish a desired negative pressure differential (or target negative pressure or setpoint) at the wound relative to the external pressure.

The circuit board 681 (including any of the circuit boards described herein) can include control circuitry, such as one or more processors or controllers, that can control the supply of negative pressure by the negative pressure source 672 according at least to a comparison between the pressure monitored by the pressure sensor 691 and the pressure monitored by the pressure sensor 692. Control circuitry can operate the negative pressure source 672 in a first mode (that can be referred to as an initial pump down mode) in which the negative pressure source 672 is activated to establish the negative pressure setpoint at the wound. The setpoint can be set to, for example, a value in the range between about −70 mmHg to about −90 mmHg, among others. Once the setpoint has been established, which can be verified based on a difference between pressure measured by the pressure sensor 691 (or wound pressure) and pressure measured by the pressure sensor 692 (or external pressure), control circuitry can deactivate (or pause) operation of the negative pressure source 672. Control circuitry can operate the negative pressure source 672 is a second mode (that can be referred to as maintenance pump down mode) in which the negative pressure source 672 is periodically activated to re-establish the negative pressure setpoint when the wound is depressurized as a result of one or more leaks in the fluid flow path, which may be caused, among other things, by an imperfect seal between the dressing and skin or tissue surrounding the wound. Control circuitry can activate the negative pressure source 672 in response to the pressure at the wound (as monitored by the pressure sensor 691) becomes more positive than a negative pressure threshold, which can be set to the same negative pressure as the setpoint or lower negative pressure.

Any of the wound dressings, wound treatment apparatuses and methods described herein may also be used in combination or in addition to one or more features described in PCT International Application No. PCT/EP2017/060464, filed May 3, 2017, titled NEGATIVE PRESSURE WOUND THERAPY DEVICE ACTIVATION AND CONTROL, U.S. Pat. Nos. 8,734,425, and 8,905,985, each of which is hereby incorporated by reference in its entirety herein.

One or more self-adhesive gaskets can be applied to the pump inlet protection mechanism 610 and pump exhaust mechanism 674 to seal the cavities 682 and 683 of the pump inlet and pump exhaust around sensors on the circuit board 681 and to seal around the exhaust mechanism vent(s) and corresponding vent(s) in the circuit board 681 (as described herein). A pre-formed adhesive sheet can be used to form the sealing gaskets between the cavities 682 and 683 of the pump inlet and pump exhaust mechanisms and sensors on the circuit board 681 and between the exhaust mechanism vent(s) and vent(s) in the circuit board 681. An adhesive can be used to seal the cavities 682 and 683 of the pump inlet protection 610 and pump exhaust mechanism 674 around sensors on the circuit board 681 and to seal around the exhaust mechanism vent(s) 684 and corresponding vent(s) in the circuit board. As described herein, the electronics assembly 600 can be embedded within layers of the dressing, such as in cutouts or recesses into which the electronics assembly can be placed.

The pump inlet protection mechanism 610 can provide a large surface area available for vacuum to be drawn by the inlet of the pump. A pump inlet (shown as rounded protrusion in FIG. 7A) can fit within a recess in the pump inlet protection mechanism 610. The pump inlet can be attached by friction fit and/or form a complementary fit to the recess of the pump inlet protection mechanism.

The pump inlet protection mechanism 610 can allow air or gas to pass through, but can block liquid from reaching the negative pressure source. The pump inlet protection mechanism 610 can include a porous material. The pump inlet protection mechanism 610 can comprise one or more porous polymer molded components. The pump inlet protection mechanism 610 can include hydrophobic or substantially hydrophobic material. Material included in the pump inlet protection mechanism 610 can have a pore size in the range of approximately 5 microns to approximately 40 microns. The pore size can be approximately 10 microns. In some cases, the pump inlet protection mechanism 610 can include a polymer that can be one of hydrophobic polyethylene or hydrophobic polypropylene. In some cases, the pump inlet protection mechanism can include a Porvair Vyon material with a pore size of 10 microns. Any of the pump inlet protection mechanism described herein can include one or more features of the pump inlet protection mechanism 610.

Extending Operational Time

In operation, the power source (which can be any of the power sources described herein) can deplete over time. If the power source capacity becomes too low, the power source may not be able to provide sufficient power level to the pump or other electronics (such as a controller). Low power source capacity can undesirably cause system malfunction, such as incorrect or unstable operation, inadequate generated negative pressure level, or the like.

It can be advantageous to detect and/or monitor the remaining capacity of the power source. If it is detected that the remaining power source capacity is at an adequate level, the NPWT system can continue to provide negative pressure wound therapy at a default negative pressure setpoint by running the pump at peak capacity. Monitoring the remaining capacity of the power source and adjusting the operation of the system based on the remaining capacity can facilitate reliable delivery of negative pressure therapy, smooth transition to the system's end of life, or the like. Monitoring the remaining capacity of the power source and adjusting operation of the system based on the remaining capacity can facilitate extended operation of the system by, for example, extending the life of the power source while maintaining adequate levels of negative pressure therapy. For example, if it is detected that the power source capacity is below a certain threshold, the system can reduce the load on the power source to maximize its remaining capacity for provision of negative pressure wound therapy via, for example, operating the pump to provide a lower level of negative pressure than the default level of negative pressure. This can be accomplished by, for instance, lowering (or making more positive) the negative pressure setpoint. If it is detected that the power source is below a minimum power threshold for adequately powering the electronics and/or the pump, the system (for example, via the controller) can shut off the pump and transition to the device's end of life (EOL) or non-operational state, in which activation the pump may be disabled.

Transition to the end of life state can be made responsive to a determination that operational lifetime of the system has been reached. For example, elapsed time since initial activation of the system can be monitored (such as, by a hardware, firmware, or software timer). In response to determining that the elapsed time satisfies a lifetime threshold, transition to the end of life state can be made. Lifetime threshold can be, for instance, 1 day or less, 2 days, 3 days, 4 days, 5 days, 6 days, 7 days, 8 days, 9 days, 10 days or more, or the like. Initial activation of the system can include one or more of pulling or removal of a pull tab (such as the pull tab 443 as shown in FIG. 4B), triggering a switch, first provision of therapy, or the like. The system can be configured to not allow provision of therapy in the end of life state (for example, by disabling activation of the negative pressure source). The system can be configured to not allow transition to any other state from the end of life state. The system can provide indication of the transition to the end of life state using any of the approaches described herein.

Indication of inadequate (or low) power source capacity can be provided to a user. Such indication can be provided visually, audibly, tactilely, and/or via communication to a remote computing device, among others. Any of the indicators described herein can be used for providing the indication. In some cases, the indication can include deactivating the source of negative pressure.

FIG. 8 illustrates a block diagram of power distribution in an electronics assembly of a NPWT system 800 (which can be any of the systems NPWT systems described herein). The NPWT system 800 includes a negative pressure source 802, a controller 804, a boost converter (or boost converter circuitry) 806 and a negative pressure source 808 (which can be any of the negative pressure sources described herein). Power is supplied from left to right in FIG. 8. As described herein, the power source 802 may include one or more batteries or other power sources. The power source 802 may provide power to both the controller 804 and the boost converter 806.

The power source 808 can supply sufficient power to power the controller 804. This power 812 can be supplied to the controller. For example, the power source 808 can provide direct current (DC) power at 3 Volts to the controller 804. The power source 808 can, in some instances, include two batteries, such as two 3V batteries with one of the batteries supplying power to the controller 804 or with both batteries supplying power to the controller 804 (for example, via a voltage divider).

In some cases, power supplied by the power source 808 may need to be increased for powering the negative pressure source 808. A boost converter (or boost regulator) 806 can be used to increase the power 814 provided by the power source 808 to a power level adequate for powering the negative pressure source 808. The boost converter 806 can include electronic circuitry configured to generate a higher level of power (for example, higher voltage of DC power) from a lower input power (for example, battery power). In some cases, the boost converter 806 can be a switched-mode power supply with at least one energy storing element (such as, an inductor or capacitor) connected to the input and, via a diode, to the output (or load), with a semiconductor switch connected in parallel with the load between the output of the at least one energy storing element and the diode. The switch can be controlled to be in a closed state to allow the at least one energy storing element to store energy (or charge). Subsequently, the switch can be controlled to transition to an open state to allow the stored energy to be supplied to the load via the diode. The fraction of time during which the switch is closed can be referred to the duty cycle of the boost converter. The duration of the duty cycle can determine the magnitude (or level) of power supplied by the boost converter. For example, longer duty cycle can facilitate storing energy in the at least one energy storing element and, as a result, greater level or power at the output. In some cases, the boost converter 806 can include a capacitor connected in parallel with the load to reduce noise (such as, higher frequency noise or ripple) in the output power.

The boost converter 806 can be a DC to DC converter with an output voltage greater than the input or source voltage. The boost converter 806 can increase or step up the level of the power source 802 to reach the level of power required for operating the negative pressure source 808. For example, the negative pressure source 808 can require power at about 30 V (or 27V or the like) to about 22 V (or lower) to operate. The boost converter 806 can increase the power level from the input 814 of the boost converter 806 (814 supplied by the power source 802) to the output 820 of the boost converter 806 (for supplying to the negative pressure source 808). As described herein, the power source 802 may include two batteries, which may facilitate a more efficient power increase (such as from 6 V provided by two 3 V batteries connected in series to 27-30 V) than with a single battery.

The controller 804 can control the boost converter 806 output by providing control signal 816. The control signal 816 can be an input power reference signal used by the boost converter 806 to adjust the output power 820. For example, the controller 804 can generate the input power reference signal via a digital to analog converter of the controller. The input power reference signal 816 can be used by the boost converter 806 to adjust the duty cycle of the boost converter, as described herein.

The controller 804 can also monitor the output generated by the boost converter 806. The controller 804 can receive boost converter output power signal 818 and control the boost converter 806 accordingly. The boost converter output power signal 818 can correspond the output power 820 of the boost converter. The boost converter output power signal, in some cases, can be a stepped down (or lower) output power 820. For example, the output power 820 can be stepped down to the boost converter output power signal 818 by being passed through a resistor. The controller 804 can compare the boost converter output power signal 818 to one or more thresholds to determine whether the output power 820 generated by the boost converter 816 is sufficient for operating the negative pressure source 808 to generate a desired negative pressure setpoint. For example, if it is determined that the output of the boost converter 806 falls below a threshold, the controller 804 can adjust the control signal 816 thereby causing the boost converter 806 to lower the output power 820. This in turn can cause the target negative pressure setpoint to be lowered (or become more positive). The controller 804 can turn off the boost converter 806 in case the output of the boost converter 806 falls below a minimum power threshold for operating the negative pressure source 808. Such adjustments to the output power 820 of the boost converter 806 by the controller 804 can prolong the life (or operational capacity) of the power source by reducing the load on the power source as its capacity is being depleted as a result of operation of the NPWT system.

The boost converter output power signal 818 can serve as a proxy for capacity of the power source 802. The controller 804 can determine the remaining capacity of the power source indirectly based on comparing the boost converter output power signal 818 to the one or more thresholds. In some cases, the controller 804 can monitor the capacity of the power source 802 directly. For example, the controller 804 can additionally or alternatively directly determine the remaining capacity of the power source 802 by comparing the power 812 supplied to the controller (or another power signal from the power source 802) to the same or another set of one or more thresholds.

In response to a determination that the capacity of the power source 802 satisfies the minimum power threshold, the controller 804 can transition to the non-operational state in which the system ceases to provide negative pressure wound therapy. In this state, activation of the negative pressure source 808 can be disabled. In some cases, the minimum power threshold can range between 10 V to 1 V, such as between 2.2 V to 1.8 V (for example, 1.9 V). As described herein, indication can be provided in response to the transition to the non-operational state of the system.

In some cases, when the controller 804 reduces the output power 820 of the boost converter 806, the load on the power source 802 is lowered. With the lowered load (for example, due to the negative pressure source 808 drawing less energy from the power source 802), the NPWT system can recover additional energy from the power source 802 and extend the life of the power source 802 and of the system. If the load is not lowered, the remaining capacity of the power source 802 may be drained at a faster rate and the power source 802 may reach its end of life faster.

In some cases, lowering the output power 820 of the boost converter 806 can indirectly cause lowering of the target negative pressure setpoint. When the output power 820 supplied to the negative pressure source 808 is reduced, the negative pressure source 808 can in turn increase the number of activations of the negative pressure source (or the duration of activations in case the activations are of varying duration) to establish or maintain the target negative pressure setpoint at the wound. As a result, a duty cycle of the negative pressure source 808, which is a measure of time the negative pressure source is active over a duration of time, can increase. The duty cycle of the negative pressure source can be monitored (for example, by the controller 804) and, in response to a determination that the duty cycle satisfies (such as, reaches or exceeds) a duty cycle threshold, the target negative pressure setpoint can be lowered. For example, the target negative pressure setpoint can be decreased from −80 mmHg (or another value) to −70 mmHg, −60 mmHg, or the like. As the target negative pressure setpoint is decreased, the power source capacity may be preserved while still maintaining the negative pressure level at the wound at an acceptable therapeutic level. Similarly, if the duty cycle of the negative pressure source decreases to no longer satisfy (such as, remain below) the duty cycle threshold, the target negative pressure setpoint can be increased (or become more negative). The duty cycle threshold can be smaller than the leak threshold described herein. For example, the leak threshold can be 50% over duration of time while the duty cycle threshold can be 30% over the duration of time.

In some cases, the target negative pressure setpoint can be decreased by larger pressure increments in response to detecting depletion of the capacity of the power source 802 (using any of the approaches described herein). For example, the target negative pressure setpoint can be decreased by −10 mmHg, −15 mmHg, −20 mmHg, or the like. For instance, the target negative pressure setpoint can be decreased from −80 mmHg to −60 mmHg. Decreasing the target negative pressure setpoint by larger pressure increment(s) can be advantageous for extending the life of power source. In some cases, because the leak rate in the fluid flow path of the NPWT system may remain substantially constant regardless of the negative pressure level provided from the negative pressure source, decreasing the target negative pressure setpoint may result in the negative pressure source being activated more often to establish or maintain the target negative pressure setpoint at the wound. Such frequent activations can result in increased duty cycle of the negative pressure source and cause a more rapid depletion of the power source. Accordingly, it may be more advantageous to decrease the target negative pressure setpoint by larger pressure increment(s) in order to preserve power source capacity.

Figure 9:
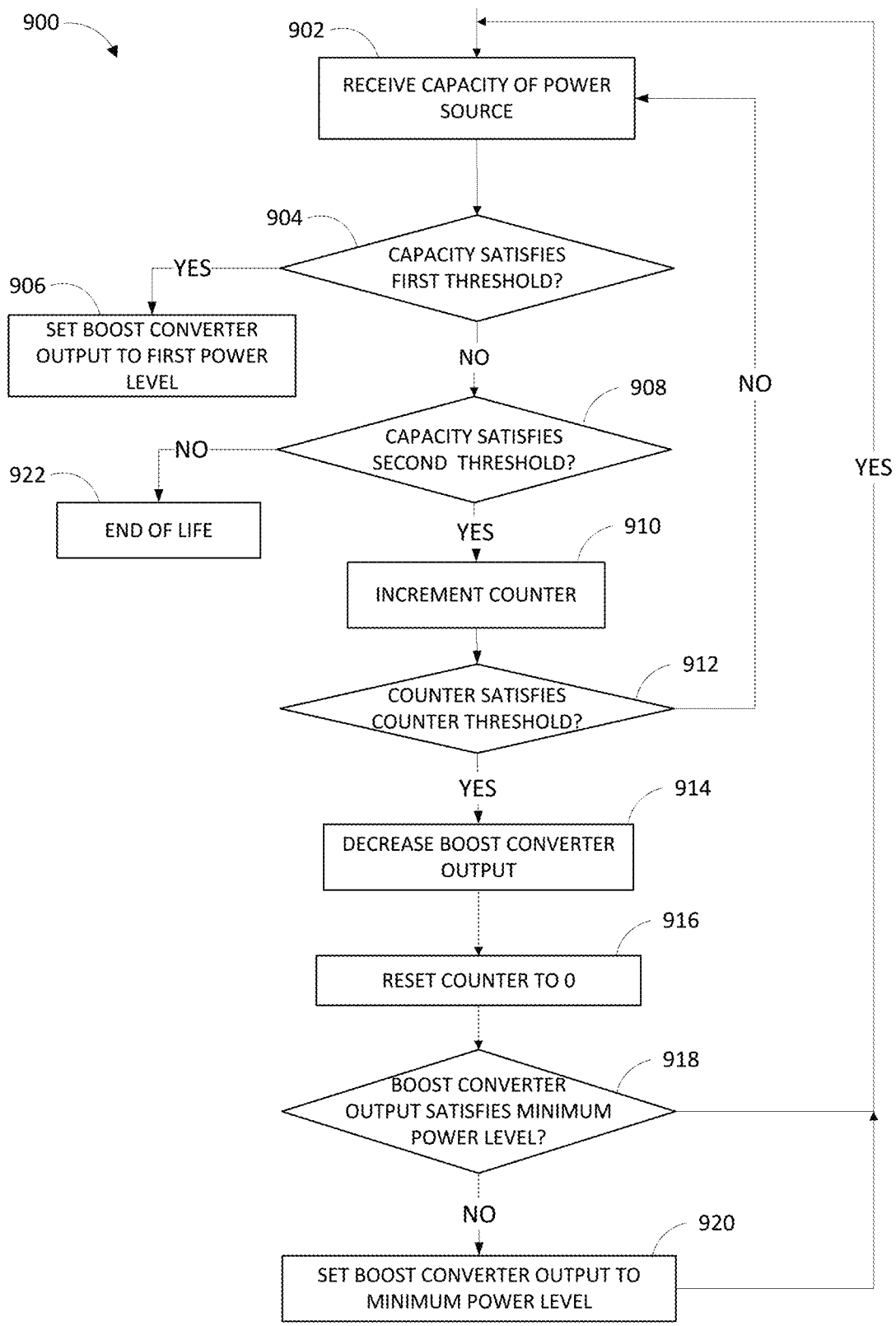
FIG. 9 illustrates a process for supplying power in a negative pressure wound therapy system.

FIG. 9 illustrates a process 900 for supplying power from the power source 808. The process 900 can be implemented by control circuitry of the NPWT system, such as by the controller 804. The process 900 can be executed periodically. In block 902, the process 900 can receive the capacity of the power source 808 using any of the approaches described herein, such as by one or more of receiving the power 812 supplied to the controller or the boost converter output power signal 818.

In block 904, the process 900 can compare the capacity of the power source 808 to a first capacity threshold. The first capacity threshold can be indicative of a power source capacity that is near its peak and has not yet been noticeably depleted. For example, for a 3 V power source, the first capacity threshold can be about 2.2 V, 2.3 V, or the like, and for 6 V power source, the first capacity threshold can be about 4.4 V, 4.6 V, or the like. As described herein, the power source 808 can include one or more batteries, such as two batteries. The process 900 can receive capacity of one of the batteries or both batteries.

At block 904, the process 900 can determine if the capacity satisfies the first capacity threshold. For example, the process 900 can determine if the capacity exceeds or equals the first capacity threshold. If so, the process 900 can transition to block 906. At block 906, the process 900 can set output power 820 of the boost converter 806 to a first power level using any of the approaches described herein, such as via adjusting the control signal 816. The first power level can be associated with the highest power output causing the negative pressure source 808 to provide negative pressure at the highest target setpoint. For example, the first power level can be between about 27 V to 30 V.

If at block 904, the capacity does not satisfy the first capacity threshold, the process 900 can transition to block 908. For example, the process 900 can determine that the capacity is less than the first capacity threshold. In block 908, the process 900 can compare the capacity of the power source 808 to a second capacity threshold. The second capacity threshold can be indicative of a power source capacity that has been noticeably depleted and is nearing the end of life. For example, the second capacity threshold for a 3 V power source can be about 1.8 V, 1.9 V, or the like, and the second capacity threshold for a 6 V power source can be about 3.6 V, 3.8 V, or the like. The second capacity threshold can be the minimum power threshold as described herein.

In block 908, if the process 900 determines the capacity of the power source 808 does not satisfy (such as, is below) the second capacity threshold, the process 900 can transition to block 922. In block 922, the process 900 can transition to the non-operational state as described herein.

If in block 908, the process 900 determines that the capacity of the power source 808 satisfies (such as, is above or equal to the second capacity threshold), the process can determine that the capacity is between the first and second capacity thresholds. This can be indicative of the power source being depleted, but still having sufficient capacity for supplying power to operate the NPWT system. Still, because the power source is depleting, the process can reduce boost converter output power (using any of the approaches described herein, such as via adjusting the control signal 816) to extend the life of the power source 808.

In some cases, the process 900 can gradually reduce boost converter output power by incrementing a counter in block 910. If in block 912 the process 900 determines that the counter satisfies a counter threshold, the process 900 can reduce the boost converter output power in block 914 using any of the approached described herein. The counter threshold can be 1, 2, 5, 10, 15, or the like. For example, if the counter threshold is 10, every ten times the capacity of the power source 808 is determined to be between first and second capacity thresholds, the boost converter output power can be decreased by one increment, such as 1 V, in block 914. For instance, the boost converter output power 820 can be decreased from 27 V to 26 V, from 26 V to 25 V, or the like in block 914. If the process 900 determines in block 912 that the counter does not satisfy the counter threshold, the process can transition to block 902.

At block 914, the process 900 can reduce the boost converter output power by one increment and transition to block 916. The increment may be 1 V, such that when the counter threshold is met, the boost converter output power is decreased by 1 V. The increment may be between 0.1 V to 5 V, such as between 0.5 V to 2 V. At block 916, the process 900 can reset the counter to zero and transition to block 918.

In block 918, the process 900 can determine if the boost converter output power satisfies a minimum power level of the boost converter. The minimum power level of the boost converter can be the lowest power level for operating the negative pressure source 808. In block 918, if the process 900 determines the boost converter output power satisfies the minimum power level of the boost converter (for example, the output is greater than or equal to the minimum power level of the boost converter), the process 900 can transitions to block 902. In block 918, if the process 900 determines the boost converter output power does not satisfy the minimum power level of the boost converter (for example, the output is less than the minimum power level of the boost converter), the process 900 can transitions to block 920. In block 920, the process 900 can set the boost converter output power 820 to a minimum output power using any of the approaches as described herein, such as via adjusting the control signal 816. For example, the minimum output power of the boost converter can be 22 V, 21 V, or the like.

Transitioning to block 920 can be indicative of the power source 802 nearing the end of life. The process 900 can transition from block 920 to block 902. Because the power source is nearing the end of life, it can be likely that after transitioning to block 902, the process would transition to block 922 as described herein. Any of the approaches for adjusting the output power of the boost converter, including the process 900, can advantageously extend the life of the power source 802 by 10% or more.

In some cases, one or more operational features of the NPWT system (such as, leak detection, blockage detection, or the like) can be disabled in response to determining the power source is being depleted. For example, NPWT system can be configured to perform leak detection for any leaks in the fluid flow path. Leak detection can involve determining whether the duty cycle of the negative pressure source measured over a duration of time satisfies (such as, reaches or exceeds) a leak threshold. The leak threshold can be any suitable number greater than zero and less than 100%, such as 50% or less or more. The duration of time can be any suitable duration, such as 10 seconds or less or more, 20 seconds or less or more, 30 seconds or less or more, 40 seconds or less or more, 50 seconds or less or more, 1 minute or less or more, or the like. In response to detecting a leak, indication can be provided using any of the approaches described herein. Negative pressure source can be deactivated in response to detecting a leak. Leak detection can be disabled to extend the life of the power source 802. For instance, leak detection can be disabled in response to determining the capacity of the power source 808 no longer satisfies one or more of the first capacity threshold or the second capacity threshold.

Figure 10:
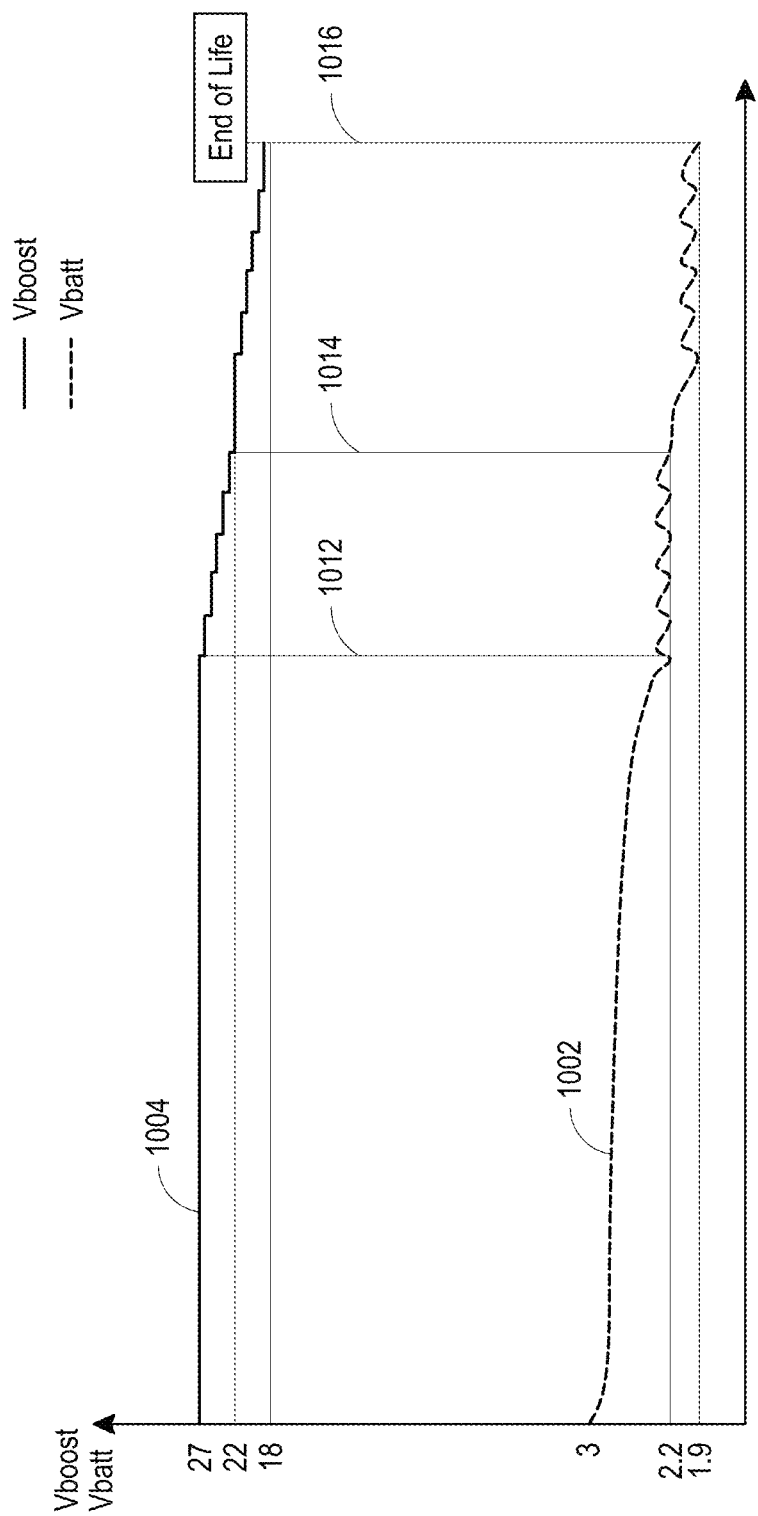
FIG. 10 illustrates a graph of adjusting boost converter power output settings in response to depletion of a power source.

FIG. 10 illustrates a graph of adjusting the output power 820 of the boost converter 816 in response to depletion of the power source 802. The graph shows the power in voltage (V) on the y-axis and the time on the x-axis. The graph shows the power of the power source (Vbatt) 1002 and the output power of the boost converter (Vboost) 1004.

Initially, as the power source 802 provides power to the electronics and the negative pressure source, the capacity of the power source (Vbatt) decreases over time from the maximum capacity (such as, 3 V) toward the first capacity threshold (such as, 2.2 V). During this period, the output power 820 of the boost converter 806 stays at a first power level (such as, 27 V). At time 1012, when the capacity of the power source no longer satisfies the first capacity threshold, but satisfies the second capacity threshold (such as, 1.9 V), the output power of the boost converter can be gradually decreased as described herein. For example, for every X amount of times (such as every 10 times) the capacity of the power source is found to be below the first capacity threshold, the boost converter output power is decreased by one increment. This can be seen in the step function observed in the curve 1004 between times 1012 and 1014. As the boost converter output power is incrementally decreased over time, the load on the power source 802 also decreases, leading to a nonlinear decrease of the power source capacity, which is illustrated by curve 1002 between times 1012 and 1014. When there is a decrease by one increment in the boost converter output power, there is a corresponding increase in the power source capacity. As shown by the curve 1002, the power source capacity fluctuates around the first capacity threshold. Life of the power source is thus extended.

As the power source 802 continues to be depleted, at time 1014, the boost converter output power 820 satisfies the minimum power level of the boost converter (such as, 22 V). As described herein, the boost converter output power can be set to the minimum power level. As illustrated, between times 1014 and 1016, this can lead to a nonlinear decrease of the power source capacity, similar to that between times 1012 and 1014. As the power source 802 continue to be depleted, the output power 820 of the boost converter continues to decrease as shown by the stepwise decrease in the curve 1004 between times 1014 and 1016. This can be due to the power source capacity being depleted, and can lead to the output power of the boost converter falling below the minimum power level of the boost converter, such as to about 18 V as is illustrated. During the period between times 1014 and 1016, the life of the power source is extended to provide the remaining capacity to powering the NPWT system. At time 1016, the capacity of the power source no longer satisfies the second capacity threshold, leading to the transition to the non-operational state and end of life.

Other Variations

While certain embodiments described herein relate to integrated negative pressure wound therapy systems in which the negative pressure source is supported by the dressing, systems and methods described herein are applicable to any negative pressure wound therapy system or medical system. For example, systems and methods for extending operational time described herein can be used in negative pressure wound therapy systems or medical systems. Such systems can be configured with the negative pressure source and/or electronics being external to the wound dressing, such as with the negative pressure source and/or electronics being positioned in a fluid proof enclosure. Additionally, the systems and methods disclosed herein can be utilized by ultrasound delivery devices, negative pressure devices powered by an external power supply (including PICO device manufactured by Smith & Nephew), negative pressure devices with a separate pump, and medical devices generally.

Any of the embodiments disclosed herein can be used with one or more features disclosed in U.S. Pat. No. 7,779,625, titled "DEVICE AND METHOD FOR WOUND THERAPY," issued Aug. 24, 2010; U.S. Pat. No. 7,964,766, titled "WOUND CLEANSING APPARATUS IN SITU," issued on Jun. 21, 2011; U.S. Pat. No. 8,235,955, titled "WOUND TREATMENT APPARATUS AND METHOD," issued on Aug. 7, 2012; U.S. Pat. No. 7,753,894, titled "WOUND CLEANSING APPARATUS WITH STRESS," issued Jul. 13, 2010; U.S. Pat. No. 8,764,732, titled "WOUND DRESSING," issued Jul. 1, 2014; U.S. Pat. No. 8,808,274, titled "WOUND DRESSING," issued Aug. 19, 2014; U.S. Pat. No. 9,061,095, titled "WOUND DRESSING AND METHOD OF USE," issued Jun. 23, 2015; U.S. Pat. No. 10,076,449, issued Sep. 18, 2018, titled "WOUND DRESSING AND METHOD OF TREATMENT"; U.S. patent application Ser. No. 14/418,908, filed Jan. 30, 2015, published as U.S. Publication No. 2015/0190286, published Jul. 9, 2015, titled "WOUND DRESSING AND METHOD OF TREATMENT"; U.S. Pat. No. 10,231,878, titled "TISSUE HEALING," issued Mar. 19, 2019; PCT International Application PCT/GB2012/000587, titled "WOUND DRESSING AND METHOD OF TREATMENT" and filed on Jul. 12, 2012; International Application No. PCT/IB2013/001469, filed May 22, 2013, titled "APPARATUSES AND METHODS FOR NEGATIVE PRESSURE WOUND THERAPY"; PCT International Application No. PCT/IB2013/002102, filed Jul. 31, 2013, titled "WOUND DRESSING AND METHOD OF TREATMENT"; PCT International Application No. PCT/IB2013/002060, filed Jul. 31, 2013, titled "WOUND DRESSING AND METHOD OF TREATMENT"; PCT International Application No. PCT/IB2013/00084, filed Mar. 12, 2013, titled "REDUCED PRESSURE APPARATUS AND METHODS"; International Application No. PCT/EP2016/059329, filed Apr. 26, 2016, titled "REDUCED PRESSURE APPARATUSES"; PCT International Application No. PCT/EP2017/059883, filed Apr. 26, 2017, titled "WOUND DRESSINGS AND METHODS OF USE WITH INTEGRATED NEGATIVE PRESSURE SOURCE HAVING A FLUID INGRESS INHIBITION COMPONENT"; PCT International Application No. PCT/EP2017/055225, filed Mar. 6, 2017, titled "WOUND TREATMENT APPARATUSES AND METHODS WITH NEGATIVE PRESSURE SOURCE INTEGRATED INTO WOUND DRESSING"; PCT International Application No. PCT/EP2018/074694, filed Sep. 13, 2018, titled "NEGATIVE PRESSURE WOUND TREATMENT APPARATUSES AND METHODS WITH INTEGRATED ELECTRONICS"; PCT International No. Application PCT/EP2018/074701, filed Sep. 13, 2018, titled "NEGATIVE PRESSURE WOUND TREATMENT APPARATUSES AND METHODS WITH INTEGRATED ELECTRONICS"; PCT International Application No. PCT/EP2018/079345, filed Oct. 25, 2018, titled "NEGATIVE PRESSURE WOUND TREATMENT APPARATUSES AND METHODS WITH INTEGRATED ELECTRONICS"; PCT International Application No. PCT/EP2018/079745, filed Oct. 30, 2018, titled "SAFE OPERTATION OF INTEGRATED NEGATIVE PRESSURE WOUND TREATMENT APPARATUSES"; each of which is incorporated by reference herein in its entirety.

Although certain embodiments described herein relate to wound dressings, systems and methods disclosed herein are not limited to wound dressings or medical applications. Systems and methods disclosed herein are generally applicable to electronic devices in general, such as electronic devices that can be worn by or applied to a user.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure.

The various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy system comprising:
    a negative pressure source configured to supply negative pressure to a wound covered by a wound dressing; and
    an electronic circuitry comprising:
        a power source configured to provide power to the negative pressure source;
        a boost converter configured to increase a level of power provided by the power source; and
        a controller configured to:
            in response to a determination that a capacity of the power source satisfies a first capacity threshold, cause the boost converter to provide power to the negative pressure source at a first power level and cause the negative pressure source to supply negative pressure to the wound at a first negative pressure level; and
            in response to a determination that the capacity of the power source does not satisfy the first capacity threshold, cause the boost converter to provide power to the negative pressure source at a second power level lower than the first power level and cause the negative pressure source to supply negative pressure to the wound at a second negative pressure level that is more positive than the first negative pressure level.

2. The system of claim 1, wherein the controller is further configured to monitor the capacity of the power source by at least one of monitoring power supplied to the controller by the power source or monitoring a power output of the boost converter.

3. The system of claim 1, wherein the controller is further configured to:
    in response to a determination that the capacity of the power source does not satisfy a second capacity threshold lower than the first capacity threshold, cause the boost converter to provide power to the negative pressure source at a third power level lower than the second power level and cause the negative pressure source to supply negative pressure to the wound at a third negative pressure level that is more positive than the second negative pressure level.

4. The system of claim 3, wherein the controller is further configured to:
    in response to a determination that the capacity of the power source does not satisfy a third capacity threshold lower than the second capacity threshold, cause the boost converter to provide power to the negative pressure source at a fourth power level and cause the negative pressure source to supply negative pressure to the wound at a fourth negative pressure level that is more positive than the third negative pressure level, the fourth power level being associated with a lowest level of power provided to the negative pressure source.

5. The system of claim 1, wherein the controller is further configured to:
    in response to a determination that the capacity of the power source satisfies a depletion threshold, transition to a non-operational state in which the negative pressure source ceases to supply negative pressure to the wound.

6. The system of claim 5, further comprising at least one indicator, wherein the controller is configured to cause the at least one indicator to indicate transition to the non-operational state.

7. The system of claim 5, wherein the controller is further configured to:
    monitor a duration of time since initial activation of the system; and
    in response to a determination that the duration of time satisfies a lifetime threshold, transition to the non-operational state.

8. The system of claim 1, wherein the controller is further configured to:
    in response to a determination that the capacity of the power source is depleting, disable detection of one or more of a leak or blockage in a fluid flow path connecting the negative pressure source to the wound.

9. The system of claim 8, wherein the controller is configured to disable detection of one or more of the leak or blockage in the fluid flow path in response to a determination that a power output by the boost converter does not satisfy the first capacity threshold.

10. The system of claim 8, wherein the controller is configured to disable detection of one or more of the leak or blockage in the fluid flow path in response to a determination that a power output by the boost converter does not satisfy a second capacity threshold lower than the first capacity threshold.

11. A method of operating a negative pressure wound therapy system, the method comprising:
monitoring a capacity of a power source configured to provide power to a boost converter that increases a level of power for operating a negative pressure source configured to supply negative pressure to a wound covered by a wound dressing,
at a first time, responsive to determining that the capacity of the power source satisfies a first capacity threshold:
causing the boost converter to provide power to the negative pressure source at a first power level, and
causing the negative pressure source to supply negative pressure to the wound at a first negative pressure level; and
at a second time, responsive to determining that the capacity of the power source does not satisfy the first capacity threshold:
causing the boost converter to provide power to the negative pressure source at a second power level lower than the first power level, and
causing the negative pressure source to supply negative pressure to the wound at a second negative pressure level that is more positive than the first negative pressure level,
wherein the method is performed by a controller of the negative pressure wound therapy system.

12. The method of claim 11, wherein monitoring the capacity of the power source is performed by at least one of:
monitoring power supplied by the power source, and
monitoring a power output of the boost converter.

13. The method of claim 11, further comprising:
at a third time, responsive to determining that the capacity of the power source does not satisfy a second capacity threshold lower than the first capacity threshold:
causing the boost converter to provide power to the negative pressure source at a third power level lower than the second power level; and
causing the negative pressure source to supply negative pressure to the wound at a third negative pressure level that is more positive than the second negative pressure level.

14. The method of claim 13, further comprising:
at a fourth time, responsive to determining that the capacity of the power source does not satisfy a third capacity threshold lower than the second capacity threshold:
causing the boost converter to provide power to the negative pressure source at a fourth power level; and
causing the negative pressure source to supply negative pressure to the wound at a fourth negative pressure level that is more positive than the third negative pressure level, the fourth power level being associated with a lowest level of power provided to the negative pressure source.

15. The method of claim 11, further comprising:
at a third time, responsive to determining that the capacity of the power source satisfies a depletion threshold, transitioning to a non-operational state in which the negative pressure source ceases to supply negative pressure to the wound.

16. The method of claim 15, further comprising causing at least one indicator to indicate transition to the non-operational state.

17. The method of claim 15, further comprising:
monitoring a duration of time since initial activation of the system; and
responsive to determining that the duration of time satisfies a lifetime threshold, transitioning to the non-operational state.

18. The method of claim 11, further comprising, responsive to determining that the capacity of the power source is depleting, disabling detection of one or more of a leak or blockage in a fluid flow path connecting the negative pressure source to the wound.

19. The method of claim 18, further comprising, responsive to determining that a power output by the boost converter does not satisfy the first capacity threshold, disabling detection of one or more of the leak or blockage in the fluid flow path.

20. The method of claim 18, further comprising:
at a third time, responsive to determining that a power output by the boost converter does not satisfy a second capacity threshold lower than the first capacity threshold, disabling detection of one or more of the leak or blockage in the fluid flow path.

* * * * *